(12) United States Patent
Panda et al.

(10) Patent No.: US 11,591,476 B2
(45) Date of Patent: Feb. 28, 2023

(54) IN-VIVO PROBE FOR REAL TIME LONGITUDINAL MONITORING OF INDUCIBLE NITRIC-OXIDE SYNTHASE IN LIVING CELLS AND ANIMALS

(71) Applicants: Koustubh Panda, Kolkata (IN); Latika Nagpal, Kolkata (IN); Brindaban C. Ranu, Kolkata (IN)

(72) Inventors: Koustubh Panda, Kolkata (IN); Latika Nagpal, Kolkata (IN); Brindaban C. Ranu, Kolkata (IN)

( * ) Notice: Subject to any disclaimer, the term of this patent is extended or adjusted under 35 U.S.C. 154(b) by 584 days.

(21) Appl. No.: 16/461,065

(22) PCT Filed: Nov. 15, 2017

(86) PCT No.: PCT/IB2017/057130
§ 371 (c)(1),
(2) Date: May 15, 2019

(87) PCT Pub. No.: WO2018/092034
PCT Pub. Date: May 24, 2018

(65) Prior Publication Data
US 2019/0309169 A1    Oct. 10, 2019

(30) Foreign Application Priority Data
Nov. 16, 2016  (IN) .............................. 201631039021

(51) Int. Cl.
*C09B 11/24*     (2006.01)
*C12Q 1/26*      (2006.01)
(Continued)

(52) U.S. Cl.
CPC ................ *C09B 11/24* (2013.01); *C09B 1/00* (2013.01); *C12Q 1/26* (2013.01); *G01N 21/6486* (2013.01); *G01N 2333/90254* (2013.01)

(58) Field of Classification Search
CPC .. C09B 11/24; C09B 1/00; C12Q 1/26; G01N 21/6486; G01N 2333/90254
See application file for complete search history.

(56) References Cited

U.S. PATENT DOCUMENTS

2001/0049109 A1* 12/2001 Lee .................. C12Q 2563/107
435/6.12
2010/0252433 A1* 10/2010 Dratz .................. C07D 311/02
204/451

OTHER PUBLICATIONS

Nagpal et al., "Mechanism of Inducible Nitric-oxide Synthase Dimerization Inhibition by Novel Pyrimidine Imidazoles," The Journal of Biological Chemistry, vol. 288, No. 27, pp. 19685-19697, DOI 10.1074/jbc.M112.446542, publ. May 21, 2013. (Year: 2013).*
(Continued)

*Primary Examiner* — Jennifer Wecker
*Assistant Examiner* — Michael Paul Shimek
(74) *Attorney, Agent, or Firm* — Nevrivy Patent Law Group P.L.L.C.

(57) ABSTRACT

The present disclosure relates to an in vivo fluorescent or radioactive probe represented by a compound of formula I which is capable of longitudinal imaging of inducible nitric oxide synthase (iNOS) expression in living cells and living animals on a real time basis. The probe of the present disclosure can exhibit specific and high affinity binding to the iNOS enzyme with reduced enzyme inhibitory property and also enables longitudinal monitoring of iNOS expression along with its activity or NO production in a same experimental subject throughout the progression of a physiological or disease process without employing separate subjects as controls and experimental. The present disclosure further provides a rapid and inexpensive real time method for visualizing iNOS expression and its activity in living cells and living animals precisely, conveniently and reversibly along with simultaneous in vivo imaging of its
(Continued)

catalytic product, nitric oxide (NO) in live physiological settings.

8 Claims, 9 Drawing Sheets

(51) Int. Cl.
    *G01N 21/64*     (2006.01)
    *C09B 1/00*     (2006.01)

(56) References Cited

OTHER PUBLICATIONS

International Search Report from Appl. No. PCT/IB2017/057130, dated Feb. 22, 2018.
Panda et al., Visualizing inducible nitric-oxide synthase in living cells with a heme-binding fluorescent inhibitor, PNAS 102:10117-10122 (2005).

\* cited by examiner

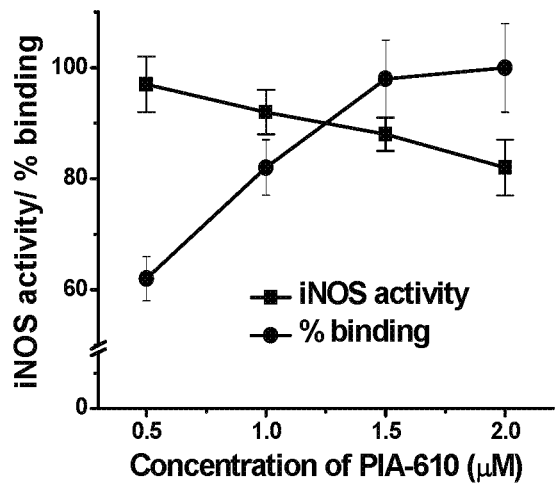
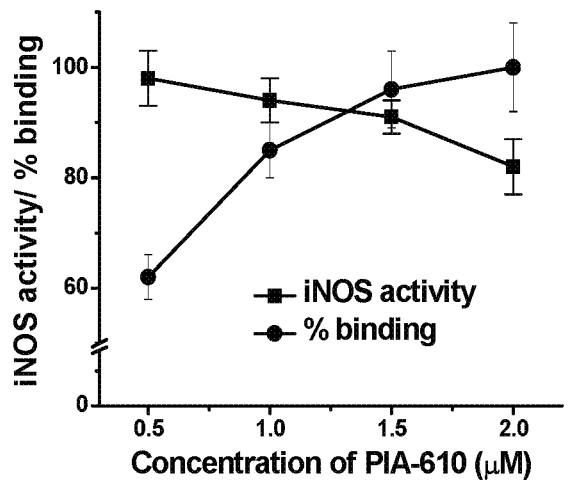
FIG. 4A  FIG. 4B
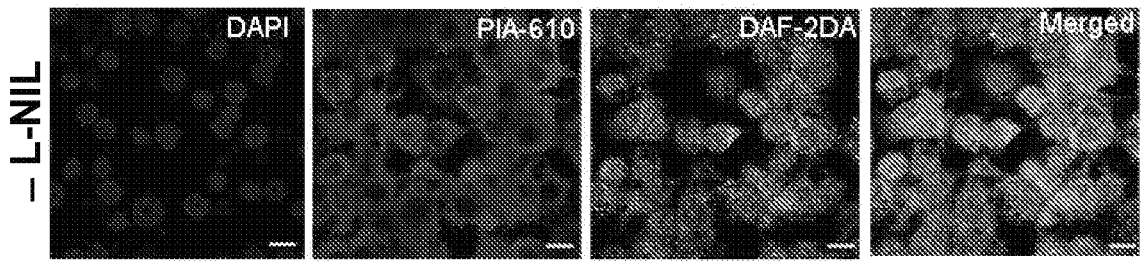
FIG. 4C
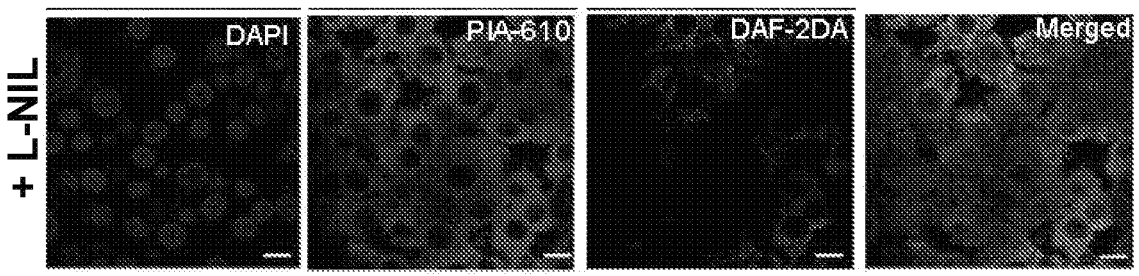
FIG. 4D

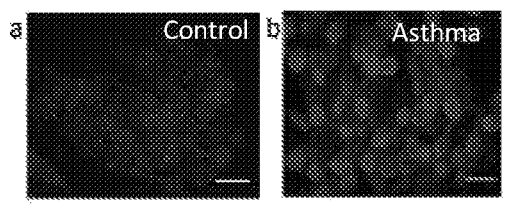
FIG. 8A
FIG. 8B
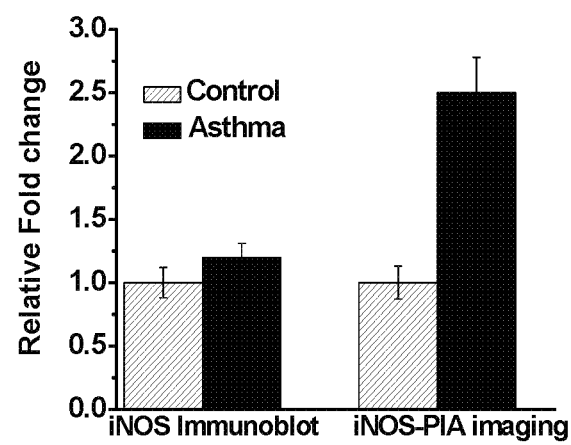
FIG. 8C

IN-VIVO PROBE FOR REAL TIME LONGITUDINAL MONITORING OF INDUCIBLE NITRIC-OXIDE SYNTHASE IN LIVING CELLS AND ANIMALS

FIELD OF THE INVENTION

The present disclosure pertains to technical field of probes for imaging live biological systems for research, diagnostic or therapeutic purpose. In particular, the present disclosure pertains to a novel in vivo probe for imaging the expression of the enzyme, inducible nitric-oxide synthase or iNOS in living cells and living animals on a real time basis, as well as a method that allows for simultaneous detection and quantification of this enzyme (iNOS), along with its activity in the form of its product, nitric oxide (NO) in biological systems using the in vivo probe for iNOS of the present disclosure along with separate in vivo probes for NO.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Nitric-Oxide Synthase (NOS) is a mammalian enzyme responsible for producing the biologically versatile compound Nitric-Oxide (NO), which plays a critical role in various life-sustaining processes like, blood circulation, memory, neurotransmission, vision and immune response. NOS, is a bi-domain enzyme which is only active in its dimeric form and utilizes arginine (Arg) as a substrate to produce the biologically active product, NO along with citrulline. NOS exists in three different forms or isoforms in the human body namely, inducible (iNOS), neuronal (nNOS) and endothelial (eNOS) to cater to different levels of NO requirement for specific physiological functions in different tissue environments. However, overproduction of NO, specifically by its inducible form, iNOS, has been etiologically linked to several inflammatory, immunological and neuro-degenerative diseases like arthritis, inflammatory bowel syndrome (IBD), asthma, sepsis, diabetes, Parkinson and Alzheimer's disease, thus making iNOS a subject of great clinical significance and interest, especially as a signature for biological inflammation.

A number of imaging techniques including those using fluorescence have been developed in the art for tracking iNOS expression and its activity in tissues, yet severe limitations exist. For instance, Panda et al, *PNAS* (2005) Vol. 102: 10117-10122, discloses a fluorescein isothiocyanate (FITC)-labeled pyrimidine imidazole conjugate, which although enables static imaging of iNOS in live cells, is however unsuitable for sustained real-time imaging of the enzyme in both cells and animals largely because of its photolability and considerable iNOS inhibition potency. Further, real time monitoring of iNOS expression in live cells and animals remains a challenge because iNOS is an unstable and short-lived enzyme (half-life of around 1.8 h) and thus liable to degeneration within the biological environment quite rapidly. The present imaging techniques employing known antibody based fluorescent probes for detection or expression evaluation of iNOS are not only time consuming but also require killing of the cells or animals making real-time assessment of quantitative expression of this short-lived enzyme along with its catalytic activity or NO producing capability virtually impossible. Moreover, the existing fluorescent probes are not capable of direct, immediate, and selective iNOS detection in live cells and animals. Genetically engineered iNOS-tagged fluorescent proteins (GFP-iNOS or RFP-iNOS) have also been used to facilitate imaging of the expression of iNOS in live cells. However, such techniques require the fusion genes to be transfected (artificially introduced into the cells) and thus cannot be used to monitor in vivo expression of the enzyme, particularly in cells and animals naturally expressing the enzyme (iNOS).

Moreover, the existing imaging techniques only allow for cross-sectional monitoring of enzyme (iNOS) expression which involves different sets of animals or cells as control and experimental. As no animal or cell can be a perfect control for any physiological or disease process, such cross-sectional techniques fail to produce both accurate as well as reproducible results. Such anomalies become critical especially when the level of expression change of the enzyme is particularly low (i.e early stages of diseases or physiological processes involving iNOS).

There is thus a need in the art for a new and improved in vivo iNOS probe that uses fluorescence, radioactivity or any imageable property for imaging the enzyme and is highly selective, highly stable, exhibits high affinity for the iNOS enzyme with reduced enzyme inhibitory property as well as enables real time longitudinal monitoring of iNOS expression along with its activity in living cells and living animals both under physiological and pathological conditions.

Moreover, as iNOS has a relatively short half-life (1.8 h), the existing methods of detection or quantification of the enzyme (i.e. Western blotting or immunofluorescence) do not deliver adequate justice to accurate evaluation of the precise level of expression change of the enzyme as they are significantly time consuming (takes several hours). However, the iNOS probe described in the present disclosure can light up the true expression of the enzyme both in cells and animals within 20 mins of its application thus allowing for rapid and more accurate assessment of the expression change of the enzyme during a physiological or disease process.

The present invention satisfies the existing needs, as well as others, and generally overcomes the deficiencies found in the prior art.

OBJECTS OF THE INVENTION

It is an object of the present disclosure to provide an in vivo probe for real time monitoring of inducible nitric oxide synthase (iNOS) expression in living cells and living animals.

It is a further object of the present disclosure to provide an in vivo probe for simultaneous or conjoint monitoring of iNOS expression along with its activity in terms of its capability to produce its catalytic product, NO (using a separate in vivo probe for NO), in living cells and living animals.

It is another object of the present disclosure to provide an in vivo probe for monitoring iNOS expression that exhibits high affinity for iNOS enzyme with reduced enzyme inhibitory property.

It is another object of the present disclosure to provide an in vivo probe for direct, immediate, and selective iNOS detection and quantification in living cells and living animals.

It is another object of the present disclosure to provide an in vivo probe for longitudinal monitoring of iNOS expression and its activity in the same experimental subject throughout progression of a physiological or disease process without employing separate subjects as controls and experimental.

It is another object of the present disclosure to provide an in vivo probe that is highly selective and enables rapid detection of iNOS expression along with its activity in living cells and living animals.

It is another object of the present disclosure to provide a method for making an in vivo fluorescent, radioactive or imageable probe.

It is another object of the present disclosure to provide a real time method for visualizing iNOS expression and its activity in living cells and living animals precisely, conveniently and reversibly.

It is another object of the present disclosure to provide a futuristic method for detecting and quantifying iNOS expression for diagnostic or therapeutic purposes of detecting inflammation or iNOS-related diseases in animals and humans using deep tissue imaging probes for iNOS (e.g. using technetium-99m, the radionuclide most commonly used as probe for imaging the human body during nuclear medicine scans).

SUMMARY OF THE INVENTION

Aspects of the present disclosure relate to an in vivo imageable probe which is capable of imaging inducible nitric oxide synthase (iNOS) expression through fluorescence in living cells or living animals on a real time basis. The probe of the present disclosure can exhibit high affinity for iNOS enzyme with reduced enzyme inhibitory property and also can enable longitudinal monitoring of iNOS expression and its activity in a same experimental subject throughout progression of a physiological or disease process without employing separate subjects as controls and experimental.

In an aspect, the present disclosure provides an in vivo probe that can be represented by following formula I:

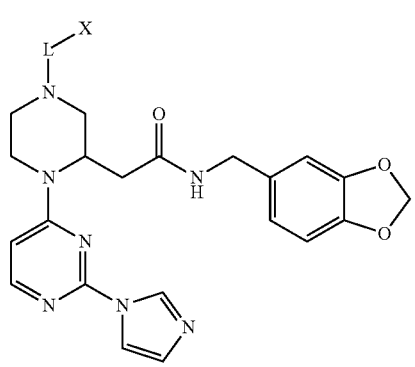

I

According to embodiments of the present disclosure, the group X of the formula I can be a chemical, fluorescent or radioisotope moiety, and L is a linker molecule which can be present or absent. The linker molecule can have substantial bulkiness or stericity that prevents compound I from entering the 'heme pocket' of dimeric iNOS to elicit its monomerization and deactivation but is at the same time capable of emitting imageable light (such as fluorescence, phosphorescence etc.) or radiation (e.g. radioisotope). In an embodiment, the group X among other fluorophores can also contain a moiety which can preferably be selected from the group consisting of Alexa Fluor dyes like Alexa Fluor-514 and Alexa Fluor-610.

In a preferred embodiment, the present disclosure provides an in vivo probe that can be represented by following formula II:

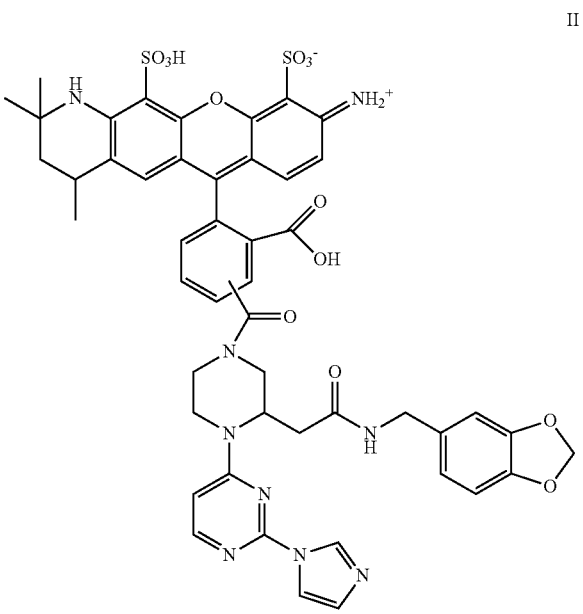

II

In another preferred embodiment, the present disclosure provides an in vivo fluorescent probe that can be represented by following formula III.

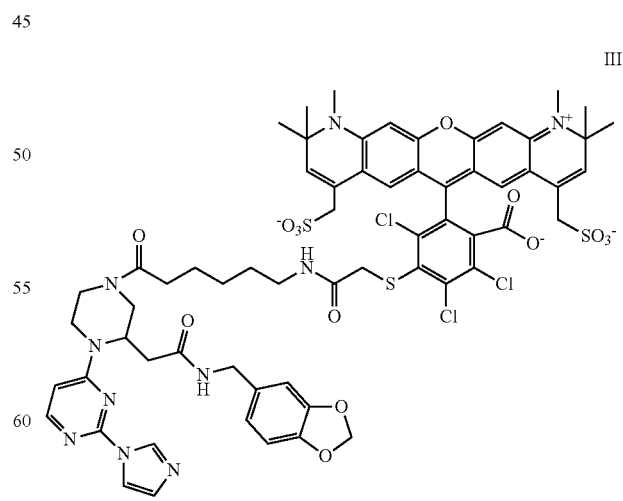

III

In another aspect, the present disclosure provides a method for producing a compound of formula II which can include the steps of:

reacting a compound of formula IV

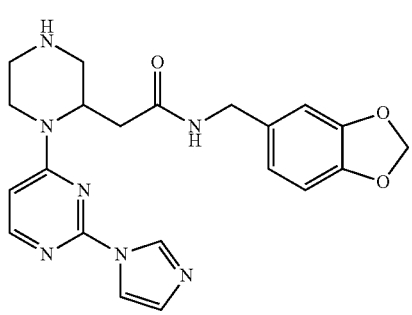

with a compound of formula V

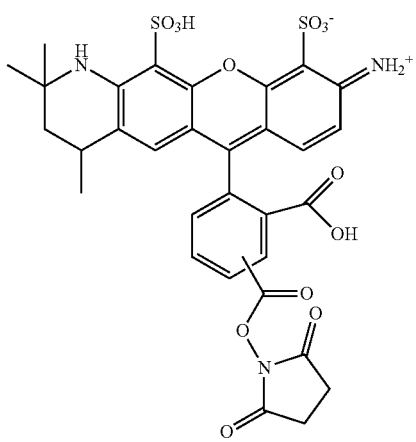

under conditions effective to produce the compound of formula II.

In another aspect, the present disclosure provides a method for producing a compound represented by formula III, which can include the steps of:

reacting a compound of formula IV

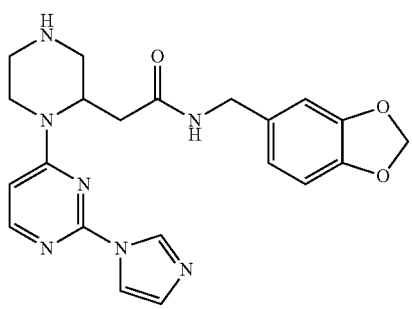

with a compound of formula VI

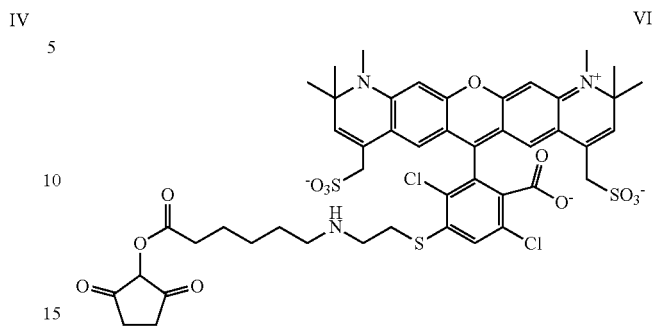

under conditions effective to produce the compound of formula III.

In yet another aspect, the present disclosure provides a method for detecting or quantifying inducible nitric oxide synthase (iNOS), or conjointly monitoring the change of iNOS expression or levels of NO produced in living cells or living animals, in which, the method can include the steps of: (a) contacting a compound of formula I of the present disclosure with the living cells or living animals; and (b) detecting emitted chemiluminescence, fluorescence, phosphorescence or radioactive radiation from the compound of formula I.

According to embodiments, the imageable probe of the present disclosure can be used for studying kinetics of enzyme reactions that involve nitric oxide release in cells, tissues or organs of a subject.

Various objects, features, aspects and advantages of the inventive subject matter will become more apparent from the following detailed description of preferred embodiments.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

FIGS. 4A-D illustrate PIA concentration dependent binding and inhibition of iNOSfl along with conjoint imaging of iNOS and NO produced in live RAW 264.7 cells using Alexa fluor 610-labelled heterocyclic derivative ("PIA-610") (red) and DAF-2DA (green) respectively, in accordance with embodiments of the present disclosure.

FIGS. 8A-C illustrate comparative evaluation of iNOSfl over expression in bronchial epithelial cells collected from the lung of normal and asthmatic human subjects through their sputum exudates using classical iNOS immunoblotting technique versus PIA based instant live cell imaging, in accordance with embodiments of the present disclosure.

DETAILED DESCRIPTION OF THE INVENTION

Figure 1A:
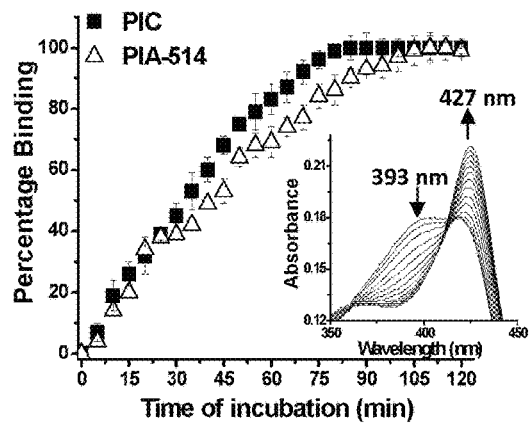
FIGS. 1A-F illustrate comparative binding affinity and inhibition potency of compound of formula IV ("PIC") and Alexa fluor 514-labelled heterocyclic derivative ("PIA-514") for purified iNOSfl (full-length iNOS) protein and fluorescence quenching and isoform specificity underlying PIA-514 binding to iNOSfl, in accordance with embodiments of the present disclosure.

The following is a detailed description of embodiments of the disclosure. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims.

Unless the context requires otherwise, throughout the specification which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The headings and abstract of the invention provided herein are for convenience only and do not interpret the scope or meaning of the embodiments.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Various terms as used herein are shown below. To the extent a term used in a claim is not defined below, it should be given the broadest definition persons in the pertinent art have given that term as reflected in printed publications and issued patents at the time of filing.

The present disclosure provides an in vivo probe which is capable of fluorescence imaging of inducible nitric oxide synthase (hereinafter referred to as "iNOS") expression along with its activity in terms of production of its catalytic product, nitric oxide (hereinafter referred to as "NO") in living cells and in living animals on a real time basis. The probe of the present disclosure can exhibit high affinity for iNOS enzyme with reduced enzyme inhibitory property and also can enable longitudinal monitoring of iNOS expression along with its activity in a same experimental subject throughout the progression of a physiological or disease process without employing separate subjects as controls and experimental.

In an aspect, the present disclosure provides an in vivo probe that can be structurally represented by following formula I:

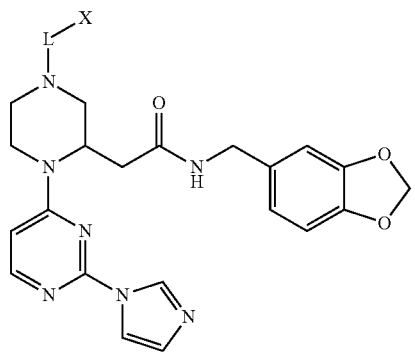

I

As shown in formula I, the probe can comprise a heterocyclic derivative as back bone that can be conjugated to a suitable fluorescence (light) or radioactive radiation emitting group (i.e. X) to form the probe. 'L' is a linker molecule which can be present or absent. The probe can bind to specific sites of the iNOS enzyme through its heterocyclic part while the light or radioactive radiation emitting group can change its emission characteristics in the course of binding of the probe to the enzyme. The probe can optionally include a linker molecule 'L' between the heterocyclic back bone and the light/radioactive radiation emitting group X to impart sufficient size, stericity or bulkiness to the probe to render the binding by the probe (I) non-inhibitory for iNOS and allow catalytic manifestation of iNOS activity (NO production capability).

In an embodiment, the group X can be a fluorophore or a radioactive element/group that can be linked to the heterocyclic derivative backbone either directly or conjugated to a specific linker with defined stericity or bulkiness through hydrogen, ionic, or covalent bonds to form the probe, I.

In a more preferred embodiment, a fluorophore or radioactive element/group can be covalently linked to the heterocyclic derivative through the piperazine moiety of the heterocyclic derivative to form the probe. The fluorophore or radioactive element/group can preferably be sterically bulky in nature or linked to the heterocyclic derivative through a sterically bulky linker or adapter of sufficient size to prevent its intrusion into the heme-pocket of the iNOS enzyme to accomplish heme binding of the probe through its imidazole moiety to adversely affect activity of the enzyme.

In an embodiment, the linker molecule 'L' can preferably be a substituted or unsubstituted benzene moiety or a group comprising more than four (04) fused benzene rings or substituent of comparable size to render the probe (I) binding non-inhibitory for iNOS.

In an embodiment, a suitable fluorophore that can be conjugated to the heterocyclic derivative can be selected from the group of commercially available bulky and robust fluors consisting of but not limited to Alexa Fluor-514 and Alexa Fluor-610.

In another embodiment, the radioactive element can include, but not limited to, technetium-99m or similar short-half life radioactive labels used for clinical imaging in humans.

In some embodiments, a linker or an adapter molecule can be used for associating the heterocyclic derivative with the fluorophore or a specific radioactive element/group, such as by connection through spacer arms or bridging molecules.

In an embodiment, the present disclosure provides an in vivo probe PIA-514 (Pyrimidine Imidazole Alexa-Fluor-514), that can be structurally represented by following formula II

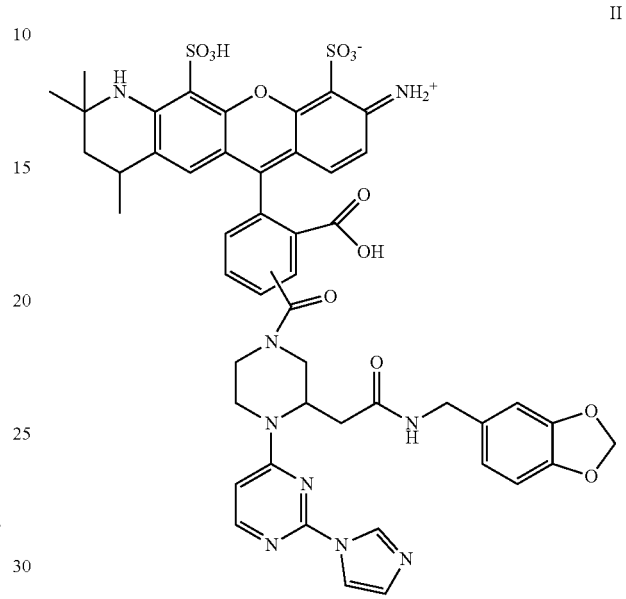

II

In a further embodiment, the present disclosure provides an in vivo probe PIA-610 (Pyrimidine Imidazole Alexa-Fluor-610), which can be represented by following formula III.

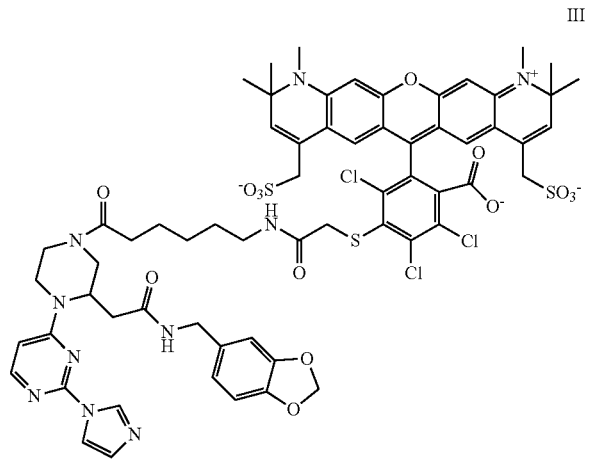

III

The probe of the present disclosure can selectively bind iNOS enzyme and produce a perceptible change in fluorescence upon binding. While the PIA-514 probe has a maximum excitation wavelength of 518 nm and emission wavelength of 540 nm, the PIA-610 probe has a maximum excitation wavelength of 610 nm against an emission wavelength of 630 nm, for which PIA-610 apparently shows superior permeability into biological tissues, and that iNOS expression in deep part of a biological tissue can be measured accurately without being influenced by environmental difference of biological tissues, auto-fluorescence originating in endogenous substances in biological tissues and the like.

The probe of the present disclosure can have a deep penetration depth and is capable of imaging iNOS expression and its activities in living cells and living animals at depths of 20 cm to 24 cm. In addition, owing to superior photostability in cells and reduced iNOS inhibition potency, the fluorescent probe of the present disclosure can enable continuous imaging of iNOS expression and its activities in living cells and living animals for an extended period of time, for instance 180 minutes or longer.

In an embodiment, the light or fluorescence emitted by the probe can be detected externally using any detection methods known in the art. In some embodiments, the change in fluorescence can be correlated to levels or amount of the NO being released in the living cells or living animals.

Unlike known probes which cause enzyme inhibition due to heme-binding, the probe of the present disclosure can exhibit high affinity towards iNOS while preventing inhibition of enzyme activity. The stericity or bulkiness of the fluorophore group located on the heterocyclic derivative and linked through the piperazine moiety can prevent the heterocyclic part to access heme through the dimer interface of iNOS through its imidazole moiety, and thereby eliminating/mitigating the problem of disruption of the active enzyme (i.e. dimer) into its monomeric form thus rendering it inactive.

The probe of the present disclosure is non-toxic and has high affinity towards the iNOS enzyme with reduced interference with activity of the target enzyme thereby making the probe an effective tool for in vivo imaging of iNOS expression along with its activity for future detection and clinical elucidation of diseases associated with over-expression of iNOS.

The probe of the present disclosure can facilitate longitudinal monitoring of iNOS expression and its activity in a same experimental subject throughout the progression of a physiological or disease process without deploying separate subjects as controls and experimental. In addition to reducing number of experimental subjects, such as animals used in the clinical studies, the probe can eliminate measurement errors arising out of inaccurate controls that are commonly encountered in cross-sectional studies.

In another aspect, the present disclosure provides a method for producing a fluorescent probe represented by a compound of formula II, wherein the process can include the steps of:
reacting a compound of formula IV

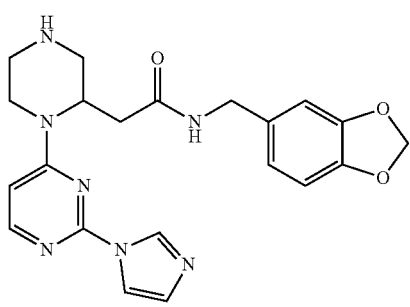

with a compound of formula V

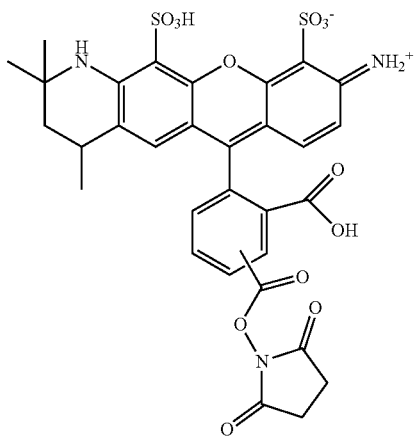

under conditions effective to produce the compound of formula II.

In another aspect, the present disclosure provides a method for producing a fluorescent probe represented by compound of formula III, wherein the process can include the steps of:
reacting a compound of formula IV

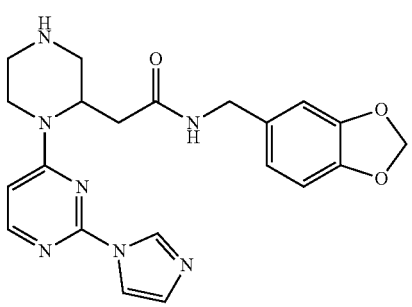

with a compound of formula VI

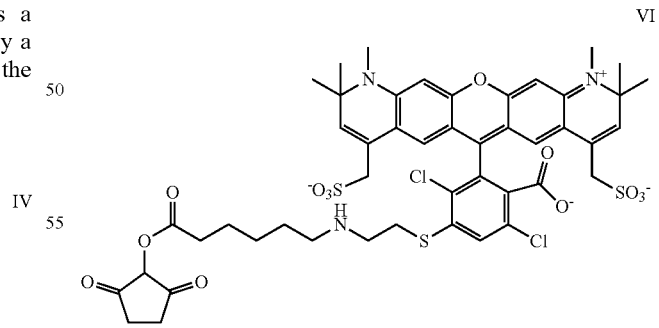

under conditions effective to produce the compound of formula III.

In yet another aspect, the present disclosure provides a method for detecting or quantifying inducible nitric oxide synthase (iNOS), along with monitoring change of NO concentration in living cells or living animals, the method can include the steps of: (a) contacting a compound of formula I of the present disclosure with the living cells or living animals; and (b) detecting emitted fluorescence from the compound of formula I conjointly with that emitted from NO detecting fluorophores (e.g DAF-2D) or imaging probes.

According to embodiments, the amount of probe required for imaging iNOS expression and its activity in living cells and living animals can vary based on route of administration and its cellular distribution. In an embodiment, an effective amount of the probe is an amount sufficient to be useful in imaging of iNOS expression and its activity, which can range from 1.5 µM-2.0 µM.

According to embodiments, the probe of the present disclosure can be used for studying reaction kinetics of nitric oxide synthase enzymes that involve nitric oxide release in cells, tissues or organ of a subject.

As used herein the term "subject" may refer to any biological system of interest. Preferably, the subject can be cultured or collected cell(s), animal subject(s) or human subject(s).

While the foregoing description discloses various embodiments of the disclosure, other and further embodiments of the invention may be devised without departing from the basic scope of the disclosure. The invention is not limited to the described embodiments, versions or examples, which are included to enable a person having ordinary skill in the art to make and use the invention when combined with information and knowledge available to the person having ordinary skill in the art.

EXAMPLES

The present disclosure is further explained in the form of following examples. However, it is to be understood that the foregoing examples are merely illustrative and are not to be taken as limitations upon the scope of the invention. Various changes and modifications to the disclosed embodiments will be apparent to those skilled in the art. Such changes and modifications may be made without departing from the scope of the invention.

Example 1: Synthesis of In Vivo Probe of the Present Disclosure

Example 1a: Synthesis of Compound Represented by Formula IV (i) Preparation of Compound 2

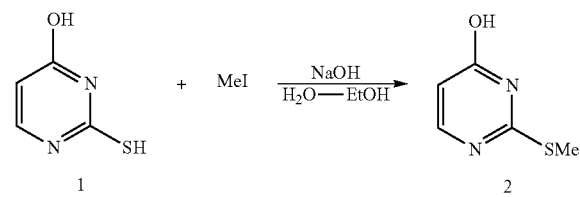

A mixture of compound 1 (1.28 gm) and NaOH (0.43 gm) was suspended in water (6 ml) and heated to 60-70° C. until the solids were dissolved. Ethanol (7 ml) and methyl iodide (MeI) (0.63 ml) were added after the solution was cooled to about 30° C. The solution was then again heated to 50-60° C. for 20 min, and then cooled to room temperature on which, white solid precipitated from the solution and it was collected by filtration. The washings were acidified with acetic acid, and the excess solvent was removed in vacuum until precipitation of white solid was observed. After filtration, the combined precipitates were thoroughly washed with water and recrystallized from ethanol to yield compound 2.

(ii) Preparation of Compound 3

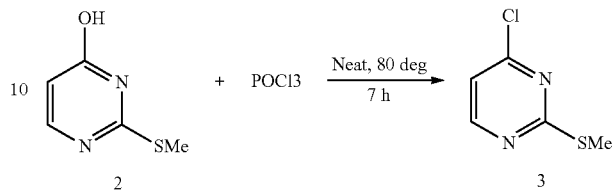

A mixture containing compound 2 (500 mg) and POCl$_3$ (2.5 ml) was heated at 80° C. under nitrogen atmosphere for 7 h. After completion of the reaction, the reaction mixture was concentrated under reduced pressure. Ice was added to the mixture and the compound was extracted with dichloromethane (DCM). The DCM layer was washed with saturated K$_2$CO$_3$ solution, dried over anhydrous Na$_2$SO$_4$ and solvent was removed to obtain a yellow colored crude product (compound 3) which was subjected for the next step without further purification.

(iii) Preparation of Compound 4

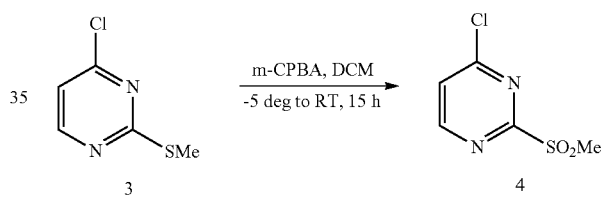

The crude compound 3 (3.52 mmol) obtained from the previous step was dissolved in DCM (14 ml) and cooled to −5° C. A solution of m-CPBA (1.214 gm) in DCM (14 ml) was added drop wise to the solution of compound 3 at −5° C. over a period of 30 min. After complete addition, the reaction mixture was allowed to stir at room temperature (RT) for 15 h. On appearance of the white precipitate, it was filtered and washed with cold DCM. The filtrate was washed with 10% K$_2$CO$_3$ twice and was dried over anhydrous Na$_2$SO$_4$. The solvent was removed to obtain compound 4 as an off-white solid.

(iv) Preparation of Compound 5

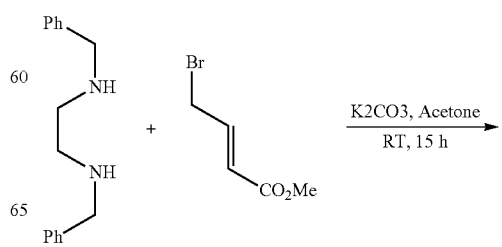

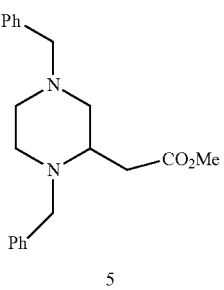

4-Bromo methyl crotonate (0.447 gm) was added dropwise at RT to a mixture of dibenzyl diamine (0.6 gm) and K₂CO₃ (0.5 gm) in dry acetone (8 ml). The reaction was allowed to stir at RT for 15 h. Acetone was removed at reduced pressure and the resulting crude compound 5 was purified by column chromatography using silica matrix and 30% ethyl acetate-hexane solution mixture.

(v) Preparation of Compound 7

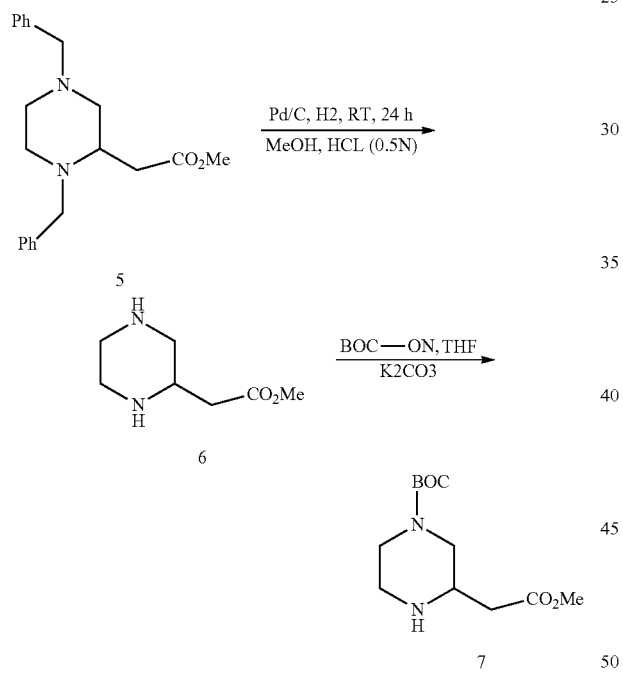

The compound 5 (0.658 g) was dissolved in MeOH (12 ml) mixed with 0.5 N HCl (10 ml). Pd/C (0.234 gm) was added to the mixture and it was allowed to stir for 24 h at RT under hydrogen gas (H₂) balloon pressure. The reaction mixture was filtered through a short silica (60-120 mesh) column to remove the Pd/C. The reaction mixture was concentrated under reduced pressure to remove most of the MeOH. The aqueous solution (approx. 2 ml) of compound 6 was made basic (checked with litmus) by slow addition of solid K₂CO₃ (0.506 gm). THF (9 ml) was added to the basic aqueous solution and it was cooled to 0° C. A cold BOC-ON (0.494 gm) solution in THF (3 ml) was added drop wise to the solution of compound 6 at 0° C. with stirring in open air. The reaction was allowed to stir at 0° C. for 1 h. Further it was stirred at RT for additional 2 h. After the completion of the reaction most of the THF was removed under reduced pressure. Then the solution was made acidic by drop wise addition of 1 M HCl (8 ml). The acidic aqueous layer was washed with DCM for two times. The DCM layer was discarded. The acidic aqueous layer was basified by pinch wise addition of K₂CO₃. The product was then extracted with DCM. The DCM layer was dried over anhydrous Na₂SO₄, and was concentrated under reduced pressure to obtain the crude compound 7 as colorless oil which was used in the next step without further purification.

(vi) Preparation of Compound 8

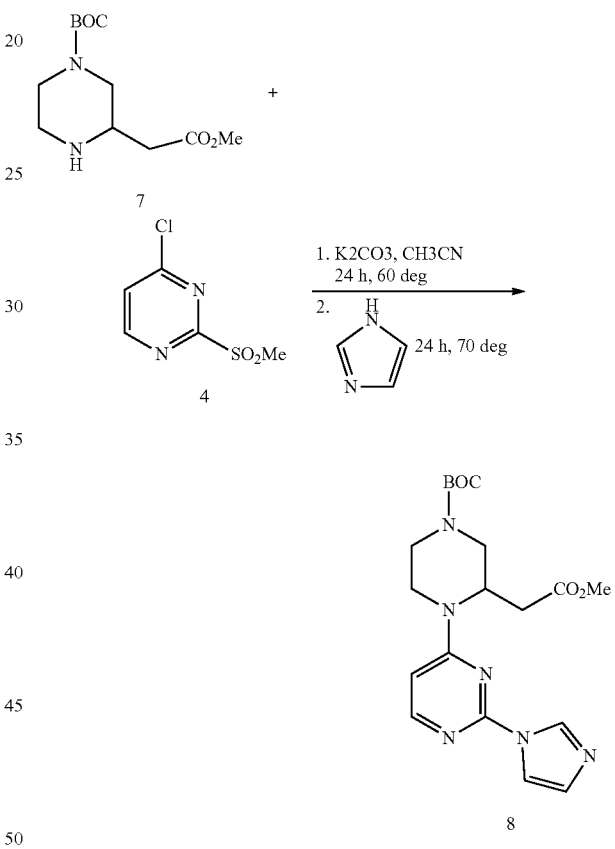

A mixture containing compounds 7 (0.241 g), 4 (0.175 g) and K₂CO₃ (0.268 g) in acetonitrile (5 ml) was heated at 60° C. for 24 h under nitrogen atmosphere. Then imidazole (0.308 g) was added to the same reaction mixture and allowed to stir at 70° C. for additional 24 h under nitrogen atmosphere. After completion of the reaction, the solvent was removed under reduced pressure. The product was extracted with DCM. The DCM layer was washed with water for 3 times, dried over anhydrous Na₂SO₄, concentrated under vacuum and was purified by column chromatography using silica and 2-4% of MeOH-DCM solvent mixture. The compound 8 was obtained as pale yellow viscous liquid.

(vii) Preparation of Compound 9

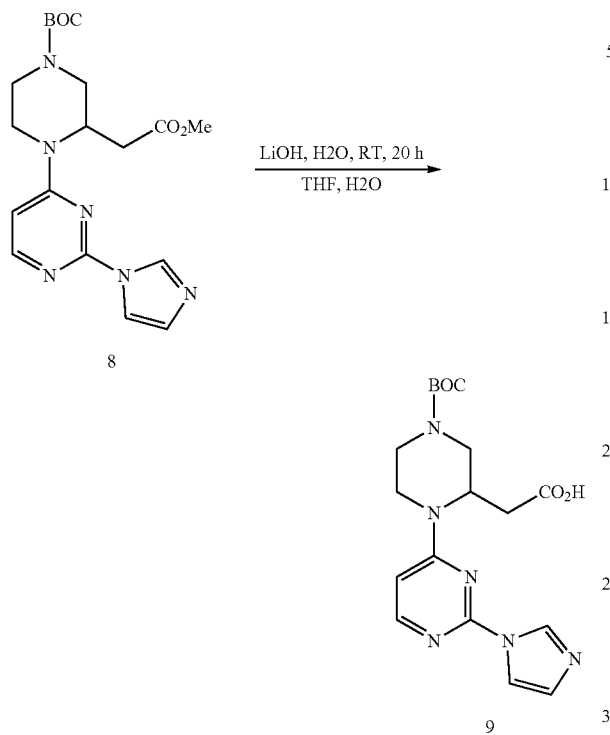

The compound 8 (0.6 mmol) was dissolved in THF (4 ml) and H$_2$O (1 ml). Thereafter LiOH.H$_2$O (0.117 g) was added to it and the reaction mixture was allowed to stir at RT for 20 h under air atmosphere. Almost all THF was removed under reduced pressure. On appearance of the white solid, it was dissolved with 3 ml of water. The aqueous layer was extracted with diethyl ether for four times. The ether layers were then discarded. The aqueous part was acidified with drop wise addition of AcOH on which the white solid again reappeared. This solid was washed with cold water followed by acetonitrile (1 ml) and diethyl ether (3 ml). It was finally dried under vacuum to yield compound 9 as a white solid.

(viii) Preparation of Compound 10

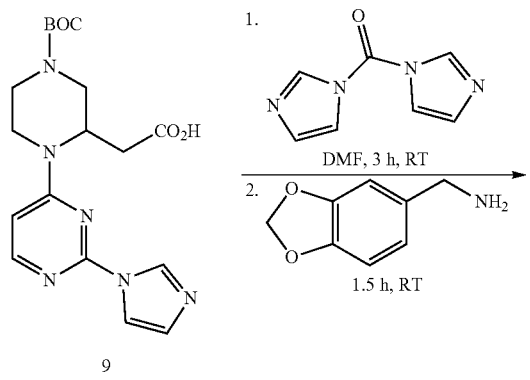

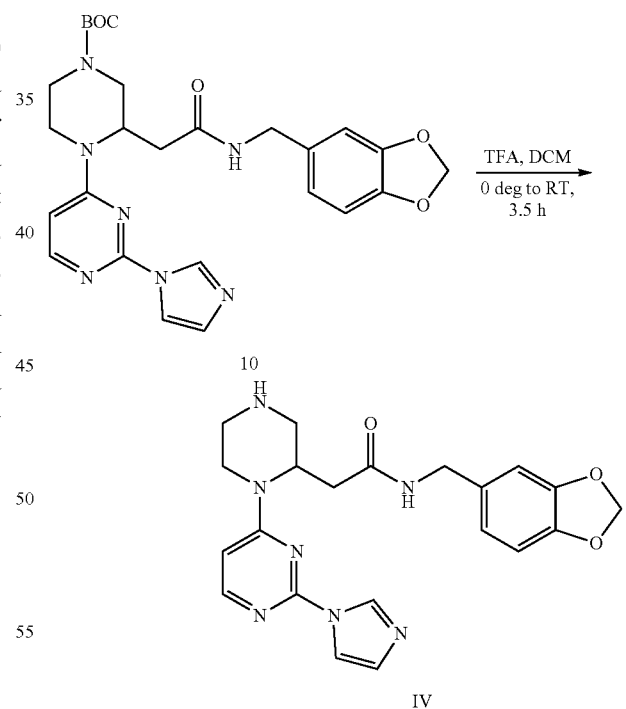

To a white suspension of compound 9 (0.129 gm) in DMF (1.5 ml), carbonyl di-imidazole (0.057 g) was added and the resultant reaction mixture was allowed to stir at RT for 3 h under nitrogen atmosphere till the solution became homogeneous in nature. Following this piperonyl amine (0.054 g) was added to the reaction mixture and allowed to stir at RT for further 1.5 h under nitrogen. After completion of the reaction, 0.1 N KOH solution (6 ml) was added and was stirred well at RT. The product was then extracted with DCM. The DCM layer was dried over anhydrous Na$_2$SO$_4$, concentrated under vacuum and the resulting crude compound 10 was directly used for the next step.

(ix) Preparation of Compound I V

The compound 10 (0.156 g) was dissolved in DCM (2 ml) and the solution was cooled to 0° C. TFA (0.5 ml) was added to the solution drop wise with stirring at 0° C. and the reaction mixture was allowed to come slowly at RT with stirring for 3.5 h. After the reaction was complete all volatiles were removed under vacuum to obtain the crude compound IV which was purified by column chromatography.

(x) Preparation of Compound IVa

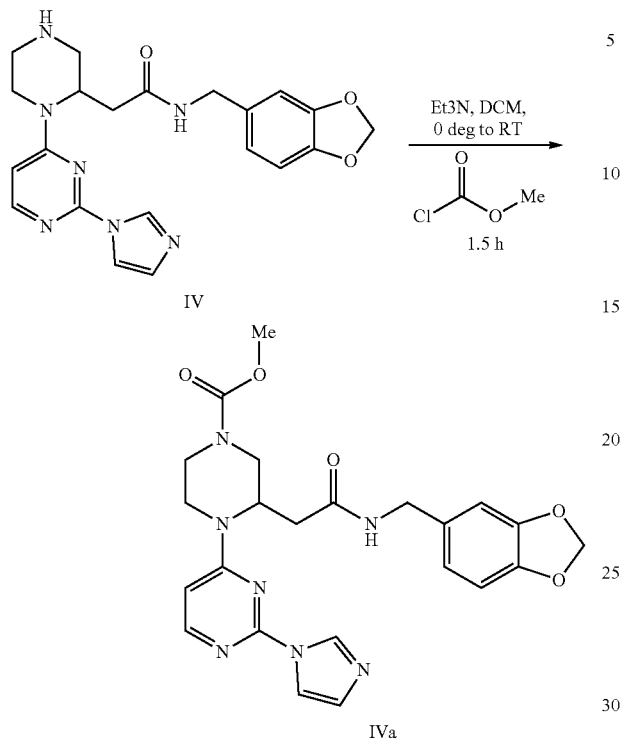

The compound IV (6.4 mg) was dissolved in DCM (10 ml, dry) and the solution was cooled to 0° C. Et$_3$N (6.2 ml, dry) was added to the solution drop wise with stirring at 0° C. Then the methyl chloroformate (2.9 ml, distilled) was added to the mixture drop wise slowly with stirring at 0° C. under argon atmosphere and the reaction mixture was allowed to come to room temperature. All volatiles were removed under vacuum and the residue was diluted with CH$_2$Cl$_2$ (20 ml). The solution was then washed with saturated NaHCO$_3$ solution (10 ml) and the organic layer was dried over anhydrous Na$_2$SO$_4$. After filtration, the solvent was removed under vacuum to obtain the crude compound IVa which was purified by column chromatography.

Example 1b: Synthesis of Fluorescent Probe Represented by a Compound of Formula II

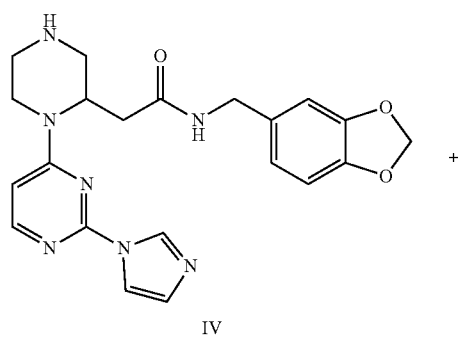

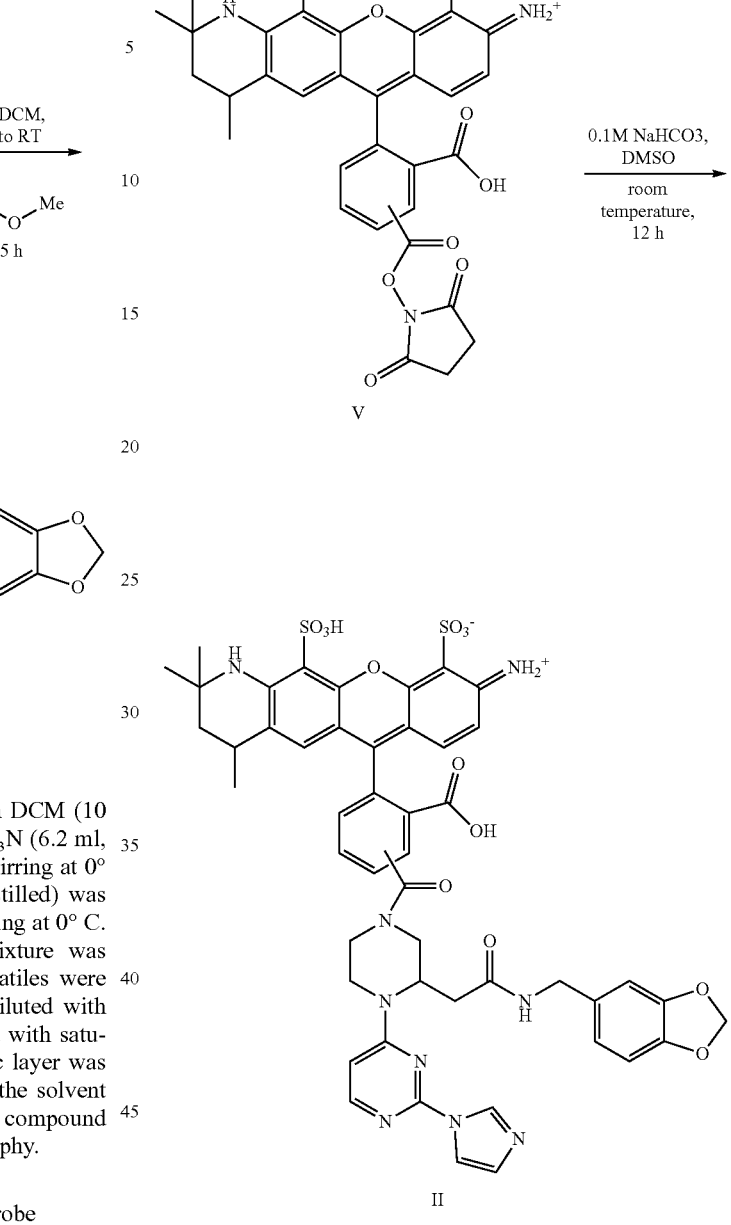

A stock solution of compound IV was prepared by dissolving compound IV (6.4 mg) in DMSO (1 ml). A small amount of stock solution (31.25 µl, 0.2 mg of compound IV) was then taken in an Eppendorf tube. A stock solution of Alexa fluor-514 was prepared by dissolving Alexa Fluor-514 (1 mg) in 0.1 M NaHCO$_3$ buffer solution (400 µl). From this stock solution, 121 µl (to maintain the 1:1 ratio of compound IV and Alexa Fluor in the reaction mixture) was added into the same Eppendorf tube under dark. The solution mixture was shaken for 12 h to complete the reaction (Checked by TLC). After the reaction, the solvent was removed by lyophilization method to obtain the compound of formula II.

Example 1c: Synthesis of Fluorescent Probe Represented by a Compound of Formula III

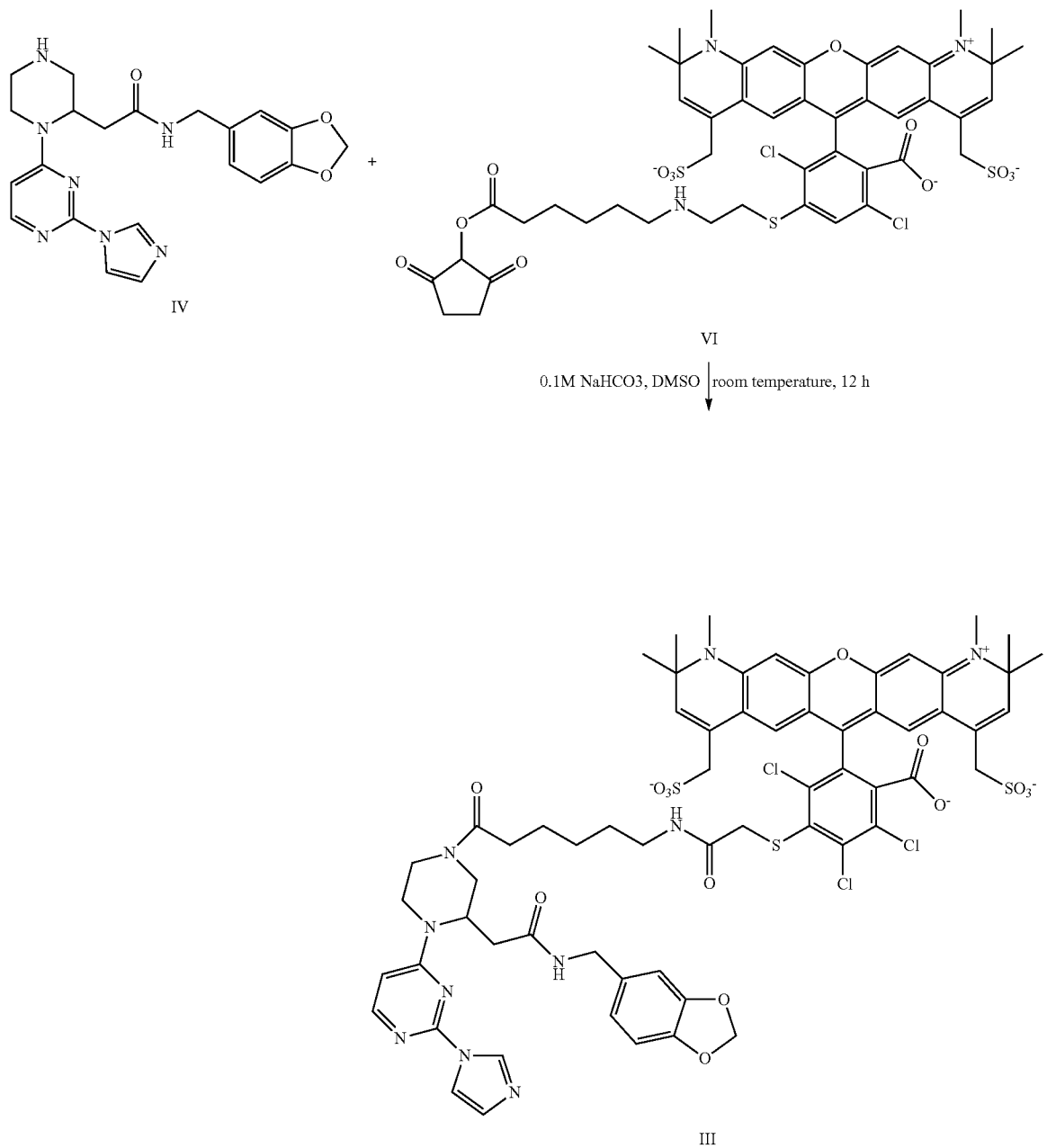

A stock solution of compound IV was prepared by dissolving compound IV (6.4 mg) in DMSO (1 ml). A small amount of the stock solution (31.25 μl, 0.2 mg of compound IV) was taken in an Eppendorf tube. A stock solution of Alexa fluor-610 was prepared by dissolving Alexa Fluor-610 (1 mg) in 0.1 M NaHCO$_3$ buffer solution (400 μk). From this stock solution 205 μl (to maintain the 1:1 ratio of compound IV and Alexa fluor in the reaction mixture) was added into the same Eppendorf tube under dark. The mixture was shaken for 12 h to complete the reaction (Checked by TLC). After the reaction, the solvent was removed by lyophilization to obtain the compound of formula III.

Example 1d: Synthesis of Adapter or Linker Molecules Fluorescent Probe Represented by a Compound Below Scheme of Synthesis of the adapter or linker molecules (with 1 to 4 benzene ring moieties) that can be used to link the probe 'X' to the nitrogen atom (N) of the piperazine moiety of Compound I in order to abrogate or mitigate its capability to monomerize and catalytically inhibit iNOS is provided as below. Adapter molecules having up to five (5) benzene rings were synthesized using the below depicted synthesis scheme and used as linkers or adapters to link the imageable probes to the piperazine moiety in Compound I.

23
24
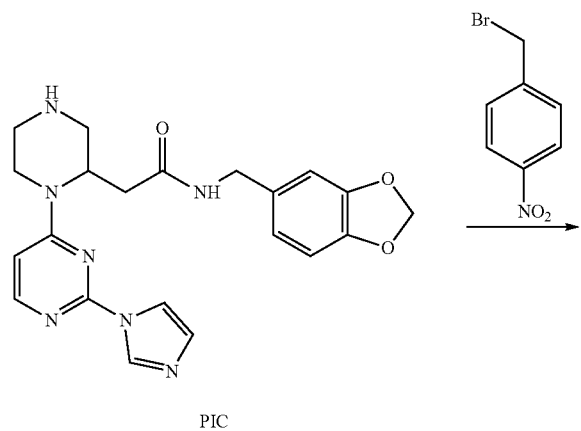
PIC
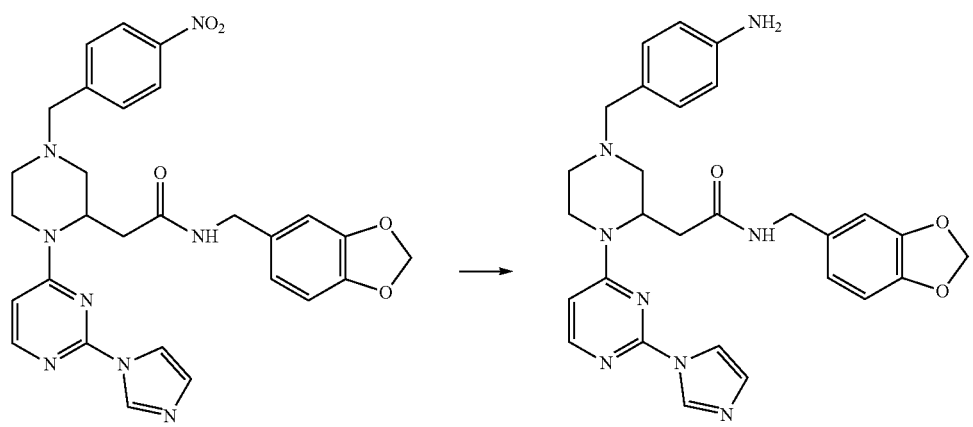
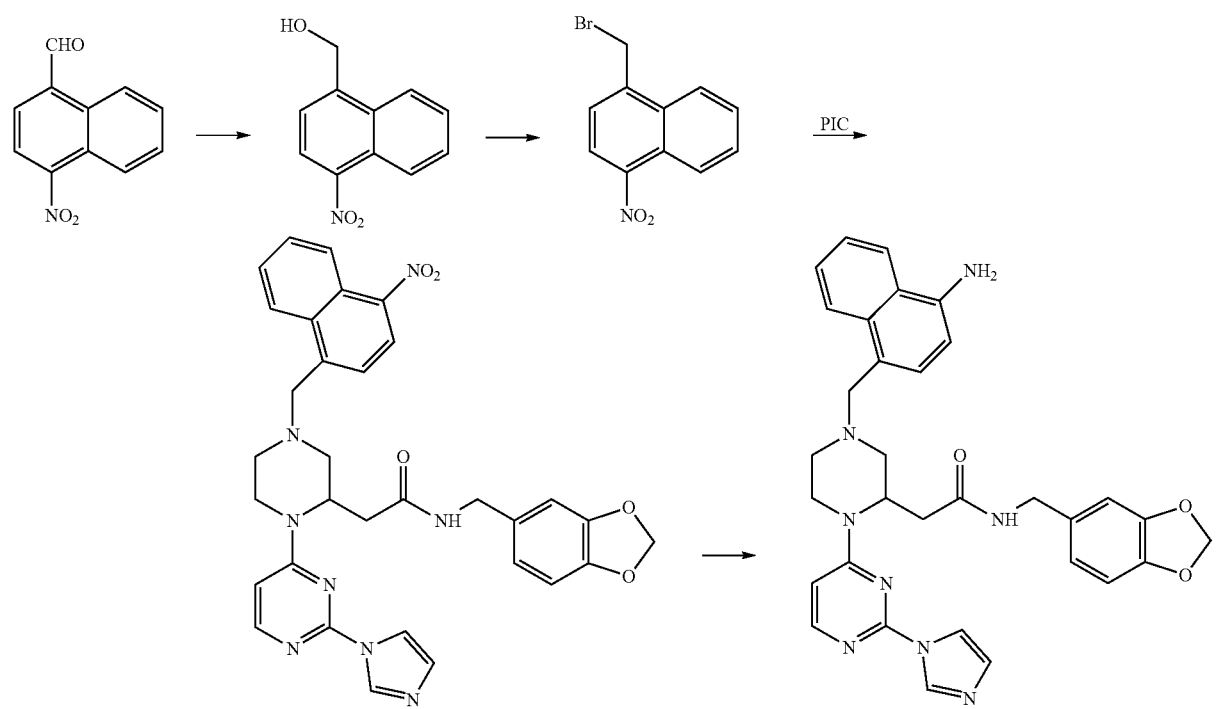
PIC 25 26
-continued
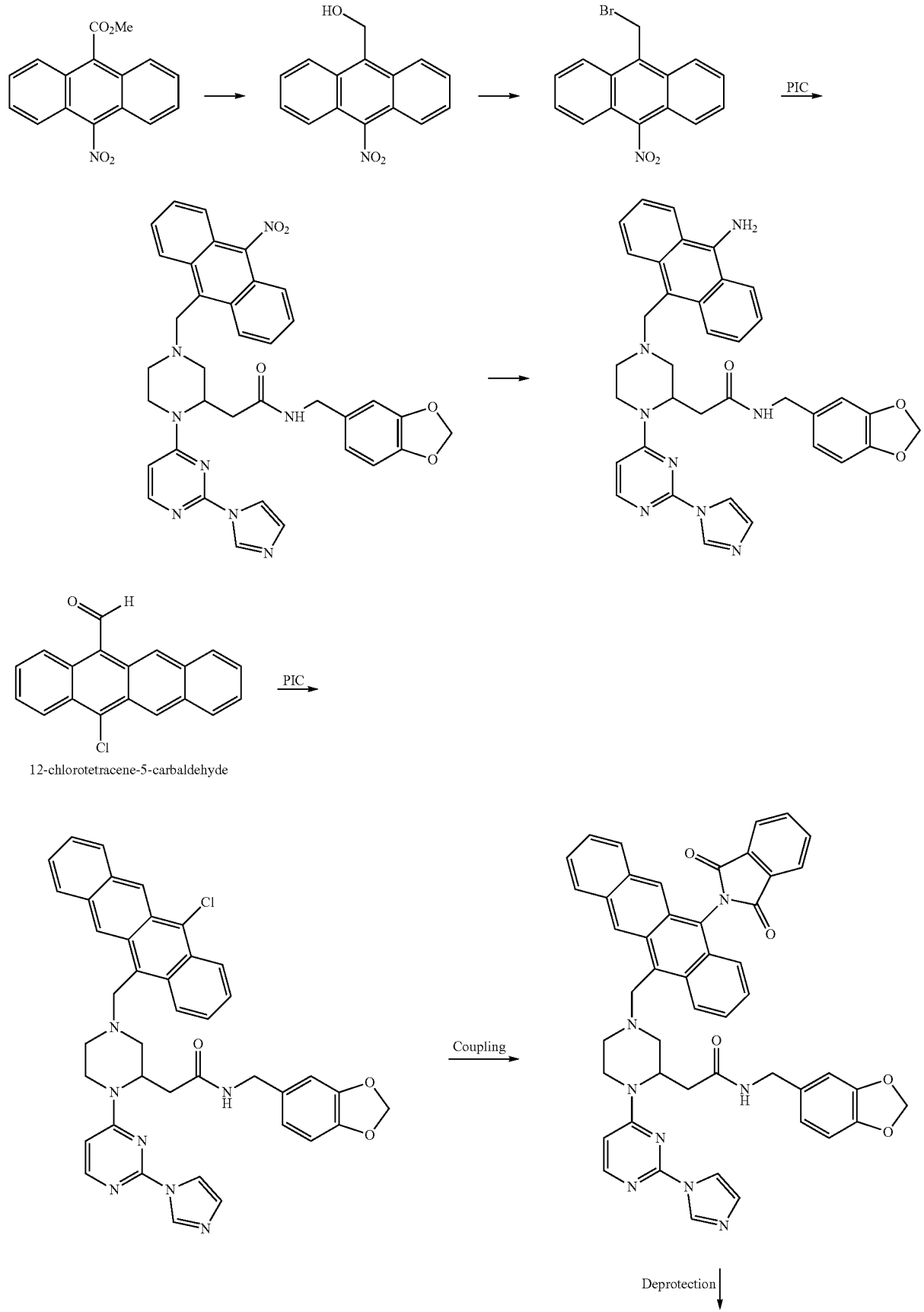

-continued

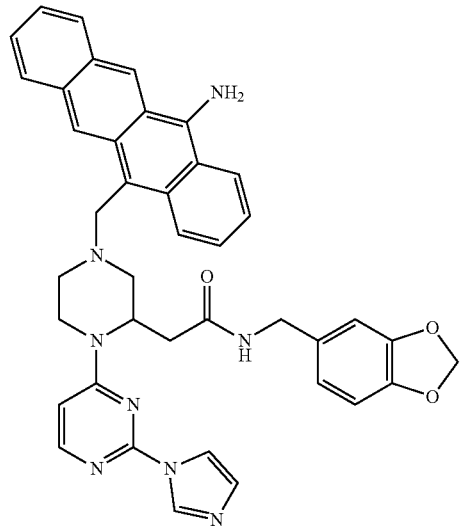

Figure 1B:
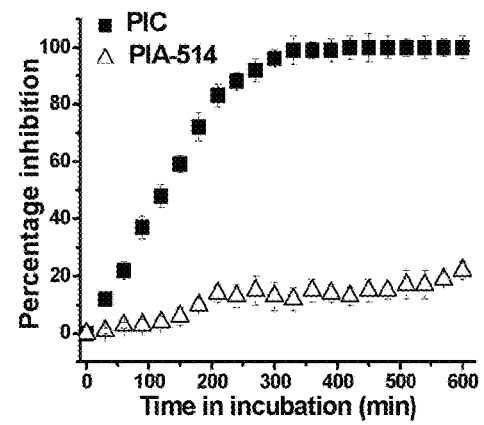
Figure 1C:
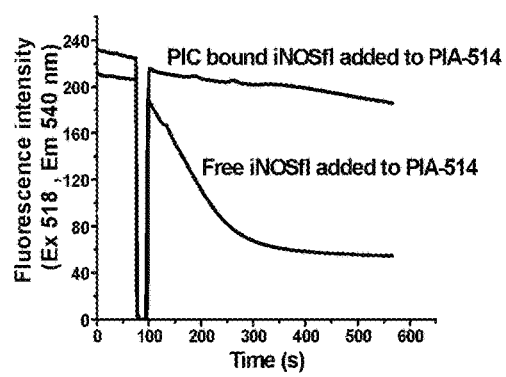
Figure 1D:
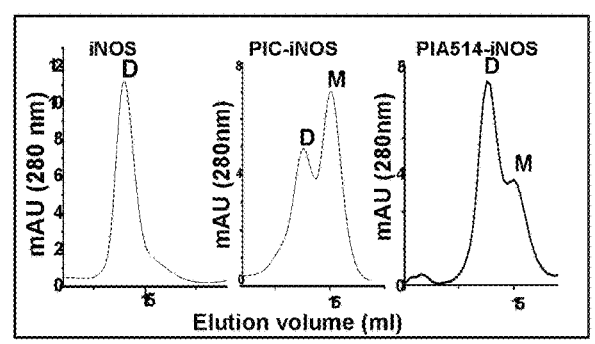
Figure 1E:
Figure 1F:
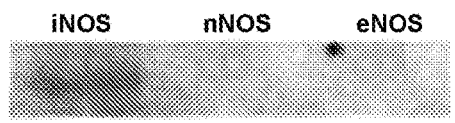

Example 2: Determination of Binding Affinity and Inhibition Potency of Fluorescent Probe of the Present Disclosure FIGS. 1A-F illustrate comparative binding affinity and inhibition potency of compound of formula IV (hereinafter referred to as "PIC") and Alexa fluor 514-labelled heterocyclic derivative (hereinafter referred to as "PIA-514") for purified iNOSfl protein and fluorescence quenching and isoform specificity underlying PIA-514 binding to iNOSfl. FIG. 1A illustrates a time dependent spectrum that was recorded after 5 µM of each compound (PIC and PIA-514) was added to 2.5 µM of purified iNOSfl. Percentage binding was evaluated in the presence of $H_4B$ (10 µM) and Arg (1 mM) from the time-dependent spectral change at 393 nm for a time-period in which no spectral change at 427 nm (indicative of monomer formation) was recorded, following addition of 5 µM of PIC & PIA-514 to 2.5 µM dimeric iNOSfl enzyme. FIG. 1B shows a percentage inhibition graph that was calculated as a function of decrease in amount of NO (in terms of total nitrite) produced by the PIC/PIA-514 bound iNOSfl protein against that produced by the free wild-type (wt) iNOSfl. FIG. 1C illustrates the change in fluorescence intensity of fixed amount of PIA-514 (0.1 µM) upon addition of excess iNOSfl enzyme (2 µM) that was either free (pure) or contaminated bound PIC. FIG. 1D illustrates Gel filtration profiles of $H_4B$ (10 µM) and Arg (1 mM) treated pure iNOSfl (complete dimer) and after treatment with PIC and PIA after 3 h of incubation. D and M indicates dimer and monomeric iNOS respectively. FIG. 1E illustrates purified proteins of the three NOS isoforms (40 µg) which were incubated with 1.5 µM of PIA-514 for 15 min and subjected to a 10% SDS PAGE. FIG. 1F shows NOS protein bands in (e) that were scanned for their possible fluorescence at Ex-520/Em 600 nm.

Figure 2:
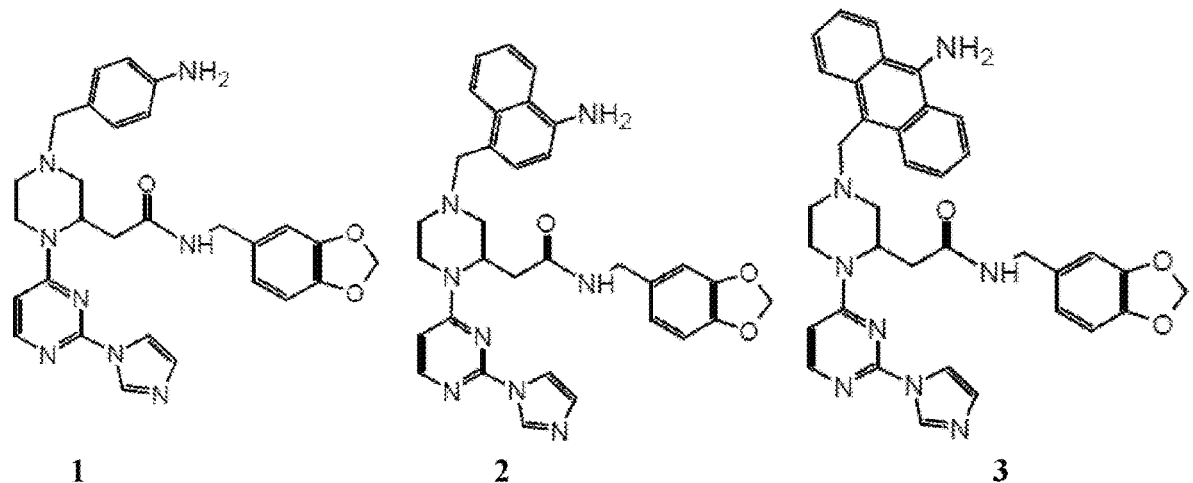
FIG. 2 demonstrates that when the substituent on the piperazine moiety of the heterocyclic group of the probe 'I' in the form of the linker 'L' or the imageable label 'X' (either directly attached to the piperazine moiety of I or through the linker L) attains or crosses a given level of 'bulkiness' or 'stericity' equivalent to four linearly fused benzene rings, the probe 'I' ceases to elicit observable catalytic inhibition of the iNOS enzyme in accordance with embodiments of the present disclosure. XO represents compound of formula IV (with 'H' attached to the piperazine nitrogen).
Figure 2:
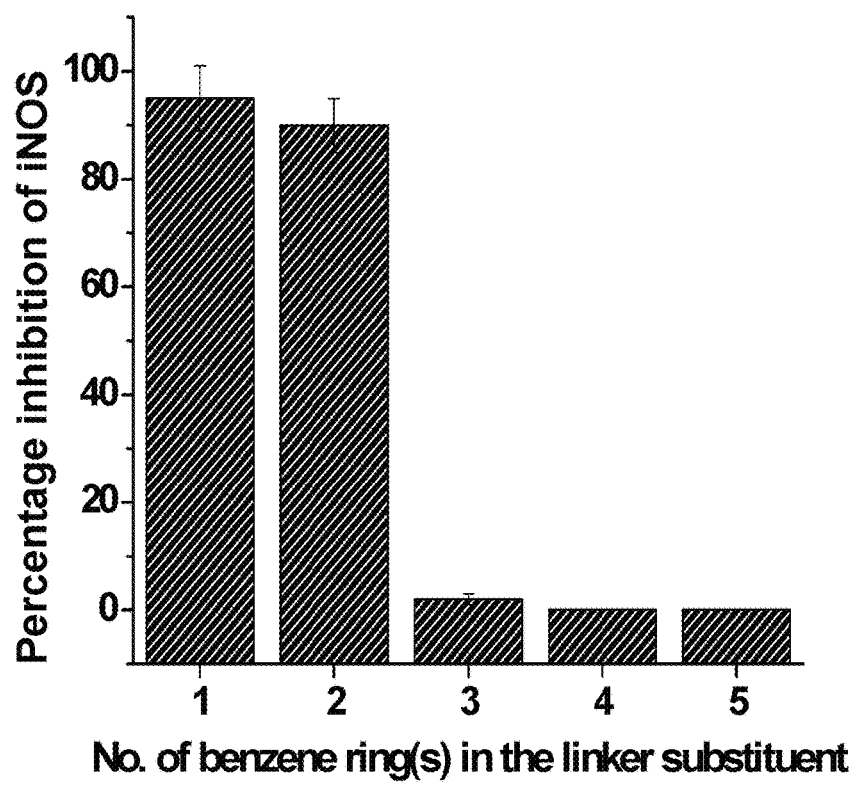

Example 3: Substitution or Labeling of the Piperazine Ring of the Probe Molecule with a Bulky Linker or Substituent Helps to Abrogate its iNOS Inhibition Potential FIG. 2 depicts the observed level of inhibition of iNOS catalytic activity when the probe I with increasing bulkiness or stericity of the Linker L (represented by one benzene ring to upto five fused benzene rings) was made to bind to the iNOS enzyme. The results clearly show that the probe I of the present disclosure virtually loses its capability to elicit catalytic inhibition of iNOS activity (measured in terms of the total nitrite produced through the Griess Reaction), when the size of L reaches or increases beyond that represented by three linearly fused benzene rings. Such results further establish that attachment of either a linker L or label X of a size bulkier or bigger than 'four linearly fused benzene rings' to the piperazine nitrogen moiety of I may assist in the abrogation of the iNOS inhibitory potential of the resultant compound or probe.

Figure 3:
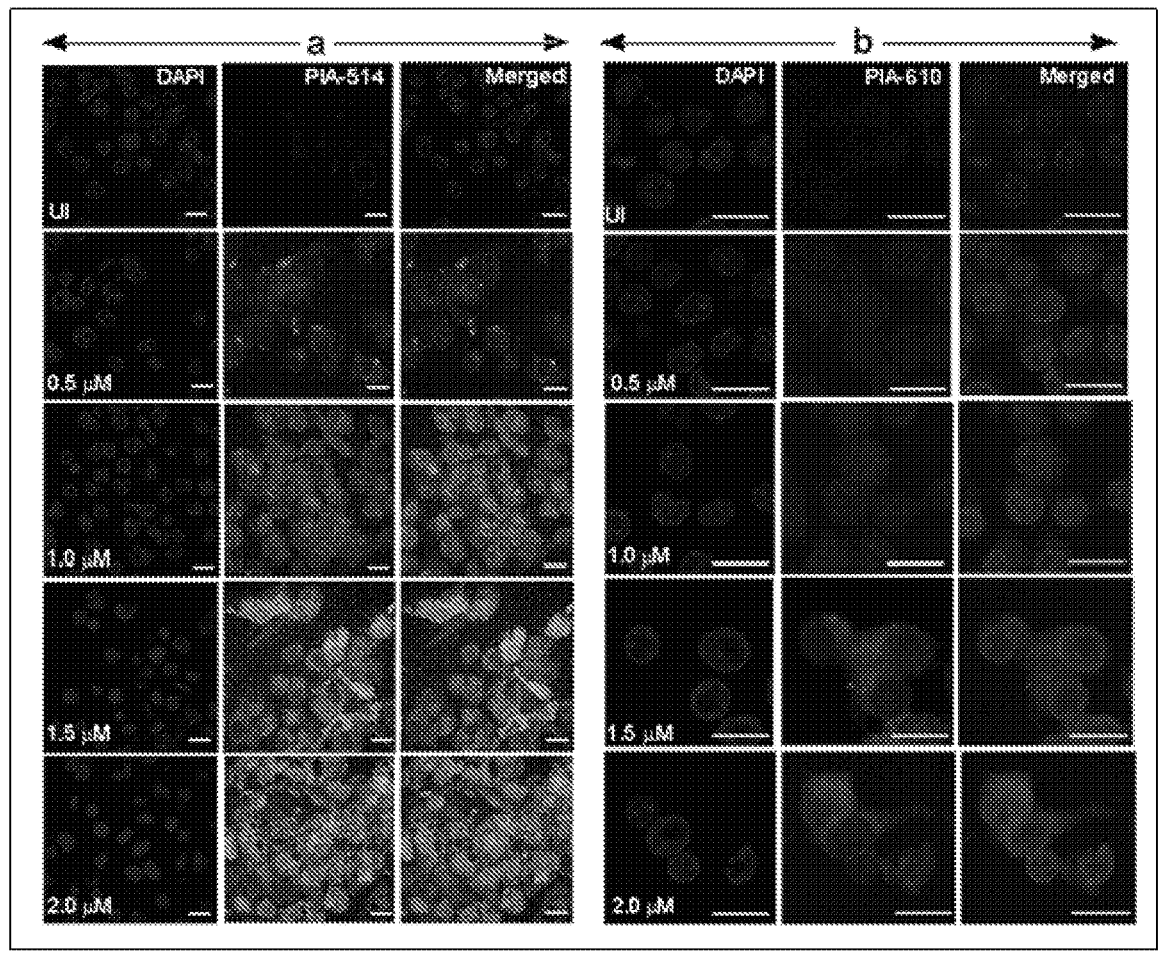
FIG. 3 illustrates the present probe i.e. compound of formula I ("PIA") concentration dependent imaging of iNOSfl in live cells using two different forms of the probe in accordance with embodiments of the present disclosure.

Example 4: Imaging of iNOS Expression and its Activity in Living Cells Using Fluorescent Probe of the Present Disclosure Experiments were carried out to determine the capability of the fluorescent probe in imaging iNOS expression and detection and quantification of nitric oxide in living cells. FIG. 3 illustrates the probe i.e. compound of formula I (herein after referred to as "PIA") concentration dependent imaging of iNOSfl in live cells using two different forms of the probe i.e. PIA-514 and PIA-610. As shown in FIG. 3, panels 'a' and 'b' demonstrate real time imaging of expressed iNOSfl in live RAW 264.7 cells with increasing concentrations (0.5 to 2.0 µM) of PIA-514 and PIA-610 respectively after 30 min of probe application (incubation). The experiment was executed following induction of iNOSfl synthesis with LPS and IFN-γ for 16 h in the RAW cells. Following treatment with the probes, the live RAW cells were further treated with DAPI (2 µl of 5 mg/ml stock solution) and were washed twice with 1×PBS and thereafter imaged under a confocal microscope. "UI" indicates Un-induced cells which were grown for 16 h without LPS+IFN-γ treatment prior to PIA application. As shown in FIG. 3a, the bar indicates 20 µm and FIG. 3b scale bar indicates 10 µm.

FIGS. 4A-D illustrate PIA concentration dependent binding and inhibition of iNOSfl along with conjoint imaging of iNOS and NO produced in live RAW cells using PIA-610 (red) and DAF-2DA (green) respectively. FIGS. 4A and 4B depict percentage of PIA-514 and PIA-610 binding and corresponding relative activity of iNOS in RAW cells at different concentrations of PIA treatment against that observed for PIA-untreated cells (as percentage activity). FIG. 4C shows simultaneous imaging of iNOSfl and NO produced in live RAW cells using PIA-610 and DAF-2DA respectively in the absence of L-NIL, a specific inhibitor of iNOS while FIG. 4D shows the same in the presence of the iNOS-specific inhibitor. Scale bars in the figure indicate 10 μm.

Figure 5:
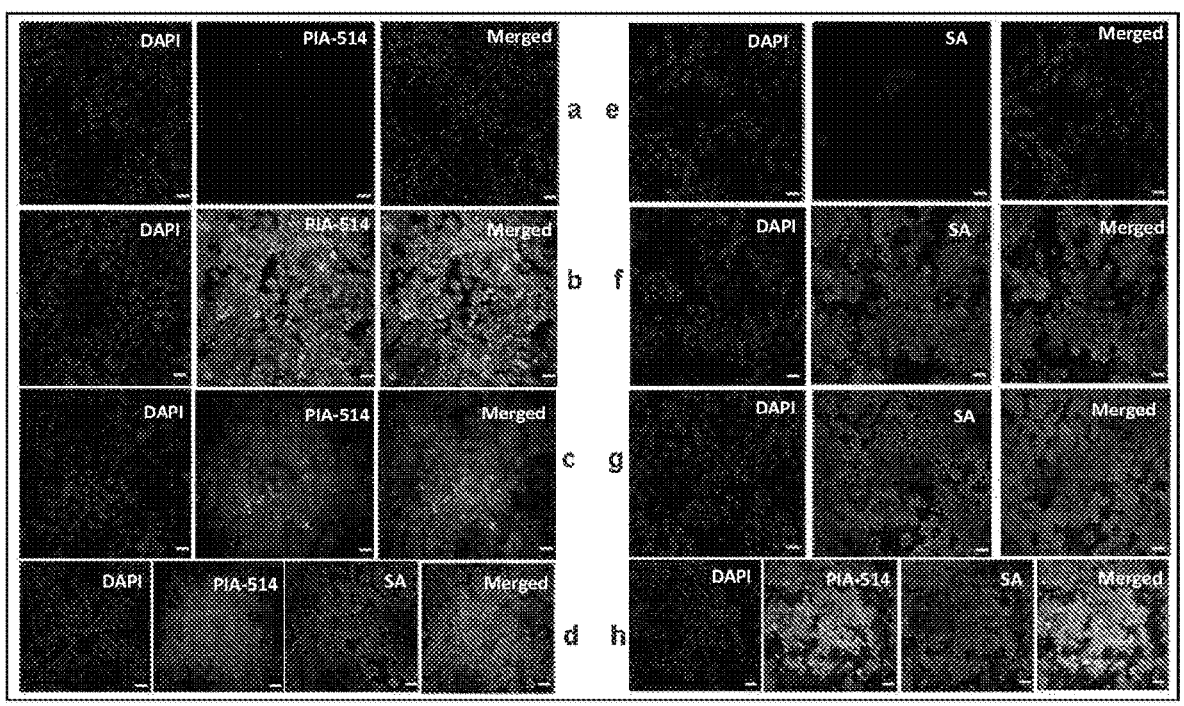
FIG. 5 illustrates specificity and differential binding of PIA to iNOSfl in the presence and absence of heme, in accordance with embodiments of the present disclosure.

FIG. 5 illustrates specificity and differential binding of PIA to iNOSfl in the presence and absence of heme. (a) Uninduced RAW cells treated with PIA-514 (1.5 μM) after 16 h of incubation with 1×PBS (14 μl) added to the cell culture medium (200 μl); (b) RAW cells induced with LPS (50 μg/ml) and IFN-γ (10 nM) for 16 h in the absence of heme biosynthesis inhibitor, succinyl acetone (SA) [250 μM] followed by treatment with 1.5 μm of PIA-514 (green) for 1 h; (c) RAW cells induced with same amount of LPS and IFN-γ as above for 16 h in the presence of succinyl acetone (SA) followed by PIA-514 (1.5 μm) treatment for 1 h; (d) RAW cells induced with LPS and INF-γ for 16 h in the presence of succinyl acetone (SA) followed by immuno-fluorescent staining using iNOS-specific primary antibody targeted against the reductase domain of iNOS (labeled red with Alexa fluor-568 tagged secondary antibody) along with PIA-514 (1.5 μM) treatment for 1 h; (e) Uninduced RAW cells immunostained with iNOS antibody (red) after 16 h of treatment with 1×PBS (14 μl); (f) RAW cells induced with LPS and IFN-γ for 16 h in absence of succinyl acetone (SA) exactly as in (b) followed by immunostaining with iNOS specific antibody (red); (g) RAW cells induced with LPS and IFN-γ for 16 h in the presence of succinyl acetone (SA) exactly as done in (c) followed by immunostaining with iNOS specific antibody (red); and (h) RAW cells induced with LPS and IFN-γ for 16 h in absence of succinyl acetone (SA) followed by iNOS immuno-fluorescent staining (red) and then incubated with PIA-514 (1.5 μM) for 1 h. All heme-deficient RAW cells were pre-conditioned for 48 h in the presence of SA to switch off their heme biosynthesis prior to induction (shown in FIG. 6). Scale bars in the figure indicate 20 μm.

Figure 6:
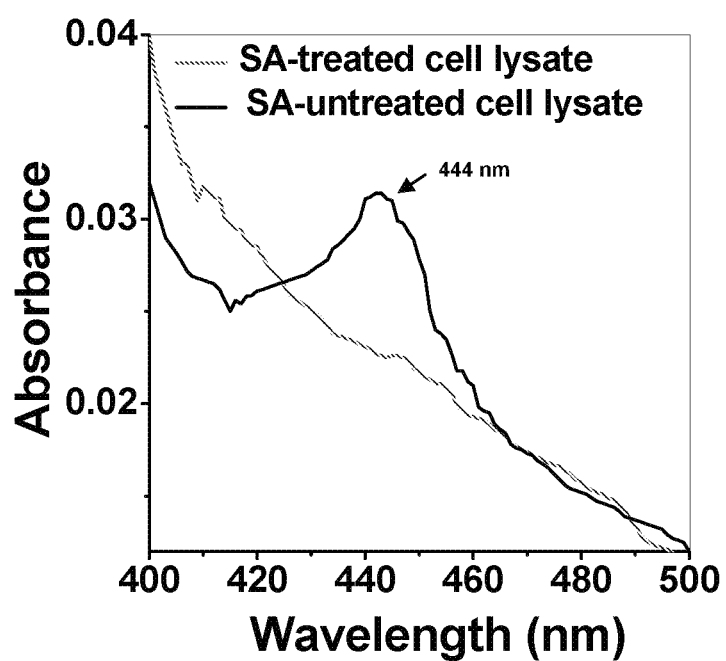
FIG. 6 is a graph illustrating heme estimation in succinyl acetone (SA) treated RAW cells, in accordance with embodiments of the present disclosure.

FIG. 6 depicts heme estimation in succinyl acetone (SA) treated RAW cells. RAW cell lysate aliquots from both succinyl acetone (SA) treated and untreated cells containing equivalent amounts of protein were reduced with dithionite and then mildly bubbled with CO gas, and then subjected to a wavelength scan (300-500 nm). The concentration of iNOS heme in the two cell populations were assessed from the resultant absorbance peaks at 444 nm to confirm heme deprivation in the SA-treated cells.

Figure 7:
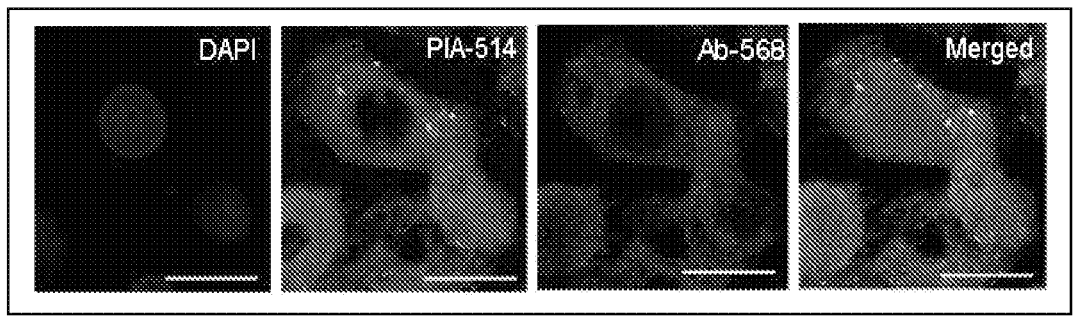
FIG. 7 is an image depicting conjoint highlighting of iNOSfl expressed in RAW 264.7 cells by PIA as well as immunofluorescent labeling using iNOS specific antibody, demonstrating iNOS specificity of PIA in accordance with embodiments of the present disclosure.

FIG. 7 depicts conjoint highlighting of iNOSfl expressed in RAW cells by PIA and immunofluorescent labeling with antibody against iNOS. Induced RAW cells expressing iNOS were fixed and simultaneously subjected to PIA (1.5 μM) labeling as well as immunofluorescent labeling with anti-iNOS antibody (targeted against the iNOS reductase domain) and anti-mouse secondary antibody tagged to Alexa fluor-568. The treated cells were imaged under a confocal microscope after washing and mounting with Vectashield containing DAPI (nuclear stain). Results show almost complete colocalization of PIA with iNOS immunofluorescence confirming precise PIA specificity for the iNOS enzyme. Scale bars in the figure indicate 10 μm. Figure represents 7.3 times of 100× magnified view of the cells shown in FIG. 5(h).

Example 5: Imaging of iNOS Expression in Live Human Cells Using Fluorescent Probe of the Present Disclosure FIGS. 8A-C illustrate comparative evaluation of iNOSfl over expression in bronchial epithelial cells collected from the lung of normal and asthmatic human subjects through classical iNOS immunoblotting technique versus PIA based instant live cell imaging. Freshly collected (live) bronchial epithelial cells (BEC) from normal and asthmatic human subjects were treated with PIA-610 (1.5 μm) for 30 min and then mildly washed with 1×PBS and instantly imaged under a confocal microscope to observe any possible change in expression of iNOSfl in the lungs of asthmatic subjects (b) against healthy controls (a), and the results have been illustrated in FIG. 8A. A simultaneously carried out immunoblot of iNOSfl using the lysates of the same BEC collected from the control and asthmatic subjects is shown in FIG. 8B. FIG. 8C shows the histogram depicting the estimated fold change in iNOS expression between normal and asthmatic lungs using the two methods. Scale bars in the figure indicate 10 μm.

Figure 9A:
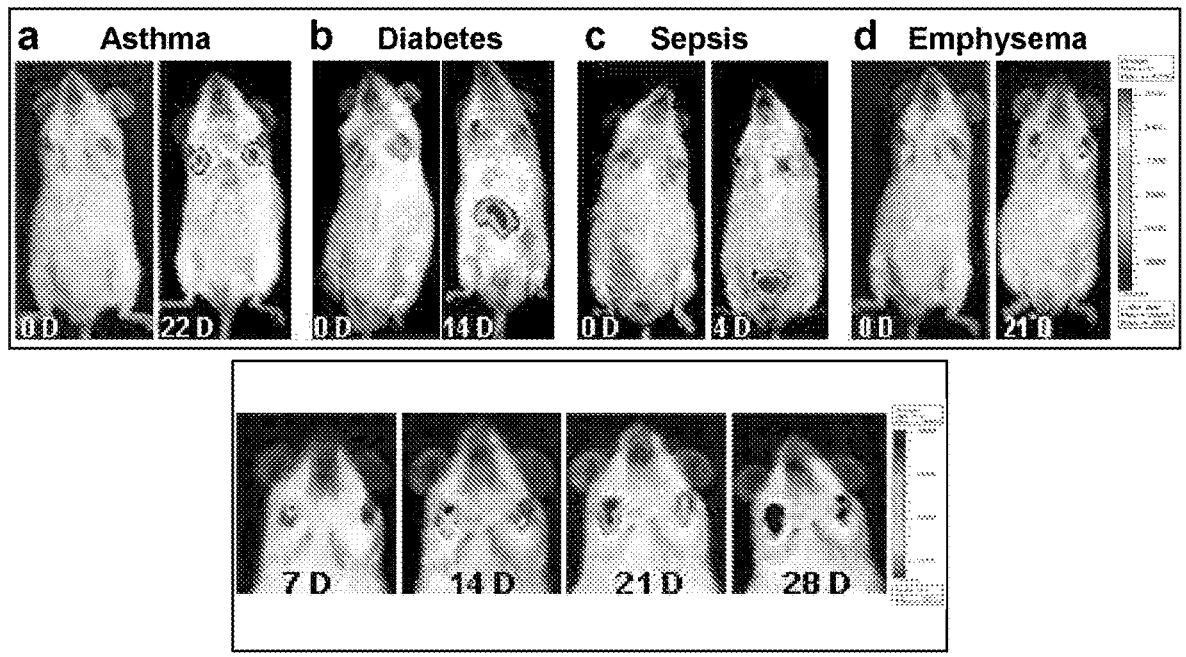
FIGS. 9A-C are images illustrating PIA as a real time probe for longitudinal monitoring of organ specific iNOS expression along with its activity or NO production capability in live diseased mice models, in accordance with embodiments of the present disclosure.
Figure 9B:
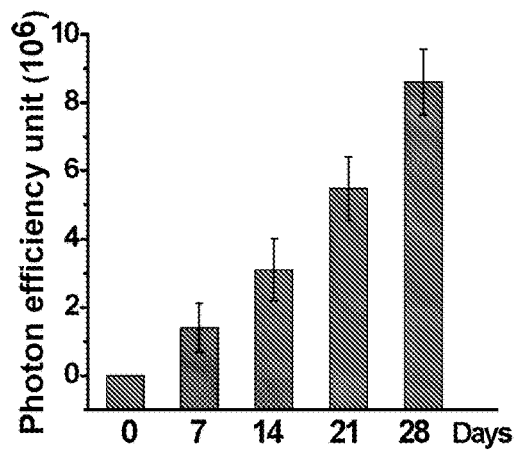
Figure 9C:
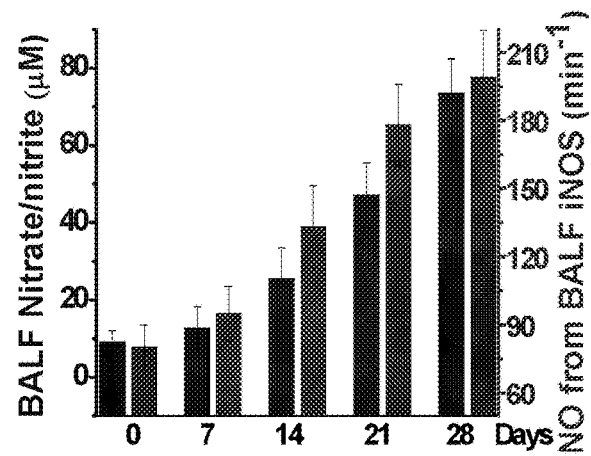

Example 6: Imaging of iNOS Expression and its Activity in Living Animals Using Fluorescent Probe of the Present Disclosure In order to investigate the capability of the fluorescent probe of the present disclosure in tissue imaging, diseased mice models were monitored. As shown in FIGS. 9A-C, live BALB/c mice were used to study the change in the over-expression of iNOS under different disease conditions. The mouse models of diseases characterized by iNOS over-expression namely, a: Asthma b: Diabetes c: Prostrate and d: Pulmonary emphysema were induced using standard protocols. Differential tissues specific iNOS expression between the control (0 day) and diseased mice are shown in Panels a-d for the indicated diseases. Panel 'e' shows the time-dependent increase in lung iNOS expression during tobacco smoke-induced pulmonary emphysema in the same mouse (longitudinal imaging) at intervals of 7 days over a total period of 28 days of tobacco smoke exposure. FIG. 9B illustrates the increase in the iNOS expression as manifested through total photon efficiency PIA-610 fluorescence. FIG. 9C depicts the lung iNOS activity as evidenced through evaluation of total lung nitrite/nitrate in the BALF (bronchoalveolar lavage fluid) collected from the live mouse immediately after being subjected to imaging after the indicated time points (i.e. 7, 14, 21, 28 days) of tobacco smoke exposure. The color coded bars on the right of panels 'd' and 'e' show the color scale of the flux density (photos/s/cm$^2$/sr) indicating the relative levels of iNOS detected through PIA-610 staining. As shown in FIGS. 9A-C, the probes (PIA) of the present disclosure can be used as a real-time probe for longitudinal monitoring of iNOS expression in live diseased mice models without separate controls.

Advantages of the Present Invention

The present disclosure provides an in vivo probe that enables longitudinal monitoring of inducible nitric oxide synthase (iNOS) expression in living cells and living animals on a real time basis.

The present disclosure provides an in vivo probe that enables rapid detection of iNOS expression and its activity in living cells and living animals within 30 minutes.

The present disclosure provides an in vivo probe that enables accurate tissue localization and quantification of iNOS in vivo.

The present disclosure provides an in vivo probe that is highly stable and thereby enables collection of imaging data real time to reveal the actual expression change of iNOS over a sustained period.

The present disclosure provides an in vivo probe that is highly cost effective.

The present disclosure provides an in vivo probe that exhibits high affinity for iNOS enzyme with reduced enzyme inhibitory property, and thereby enables accurate detection and quantification of iNOS expression in living cells and animals.

The present disclosure provides an in vivo probe that facilitates simultaneous monitoring of iNOS expression and its activity (NO production) in living cells and animals.

The present disclosure provides an in vivo probe that facilitates longitudinal monitoring of iNOS expression in a same experimental subject throughout progression of a physiological or disease process which eliminates the need of separate subjects as controls and experimental, thus removing errors arising out of inaccurate controls.

The present disclosure provides a target specific and highly efficient in vivo probe which highlights iNOS expression with very less quantity compared to known fluorescent probes.

The present disclosure provides a method for visualizing iNOS expression along with its activity in living bodies precisely and conveniently on a real time basis.

We claim:

1. A compound represented by following formula I:

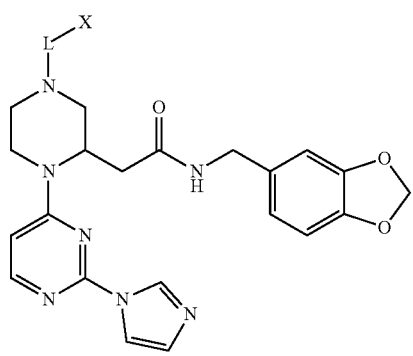

I wherein X is Alexa Fluor or a radioactive tracer element and L is absent or a linker molecule selected from a group comprising substituted or unsubstituted aryl having four or more fused benzene rings, with a proviso that when X is a radioactive tracer element, L is a linker moiety selected from a group comprising substituted or unsubstituted aryl having four or more fused benzene ring, wherein the compound is substantially unable to elicit inhibition of the inducible nitric oxide synthase (iNOS).

2. The compound of claim 1, wherein the radioactive tracer element comprises technetium-99m or other radioactive labels of short half-life permissible for human use.

3. The compound of claim 1, wherein the Alexa Fluor is selected from the group consisting of Alexa Fluor-514 and Alexa Fluor-610.

4. The compound of claim 1, wherein said compound is represented by following formula II:

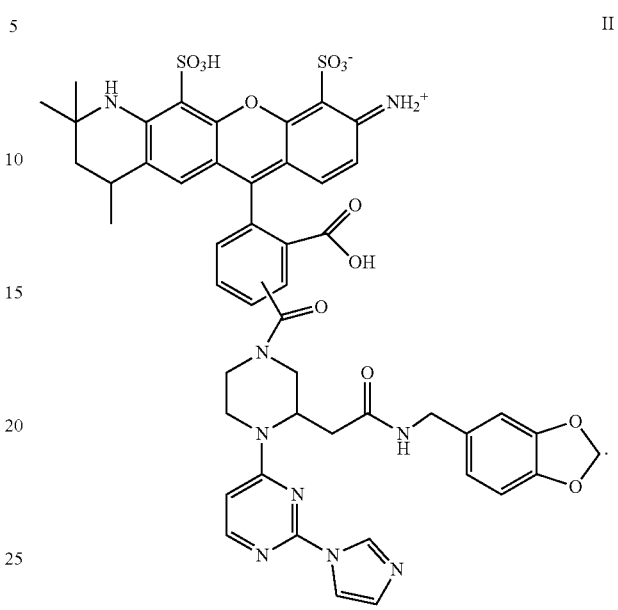

II

5. The compound of claim 1, wherein said compound is represented by following formula III:

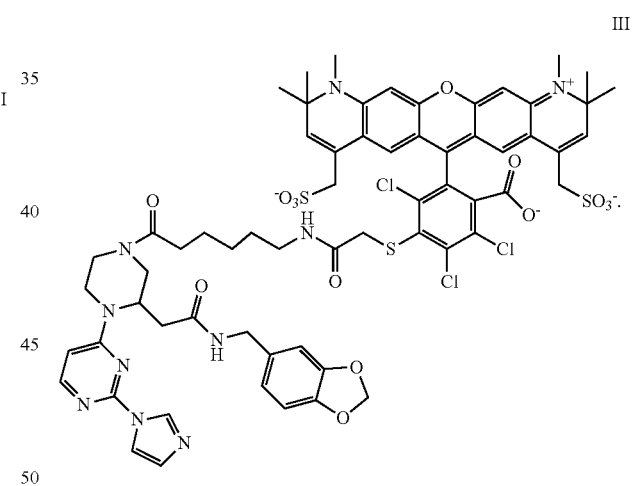

III

6. An in-vivo method for conjointly detecting or quantifying inducible nitric oxide synthase (iNOS) along with its product, nitric oxide (NO), or for monitoring change of NO concentration in a living cells or a living animals, the method comprising the steps of:

(a) administering a compound of formula I according to claim 1 to the living cells or living animals, said compound being substantially unable to elicit inhibition of the inducible nitric oxide synthase (iNOS); and (b) detecting emitted chemiluminescence, fluorescence, phosphorescence, or radioactive radiation from the compound of formula I through imaging of said living cell or living animal.

7. Use of compound of formula I according to claim 1 for studying kinetics of enzyme reactions that involve nitric oxide release in cells, tissues, or organs of a subject.

8. The use of compound of formula I according to claim 6, wherein the subject is any of: a cultured cell, a collected cell, an animal, and a human.

\* \* \* \* \*